US007429656B2

(12) United States Patent
Kung et al.

(10) Patent No.: US 7,429,656 B2
(45) Date of Patent: Sep. 30, 2008

(54) INHIBITION OF SARS-ASSOCIATED CORONAVIRUS (SCOV) INFECTION AND REPLICATION BY RNA INTERFERENCE

(75) Inventors: Hsiang-Fu Kung, Hong Kong (CN); Ming-Liang He, Hong Kong (CN); Bo-Jiang Zheng, Hong Kong (CN); Yi Guan, Hong Kong (CN); Marie Chia-Mi Lin, Hong Kong (CN); Ying Peng, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 44 days.

(21) Appl. No.: 11/452,267

(22) Filed: Jun. 14, 2006

(65) Prior Publication Data

US 2006/0258611 A1 Nov. 16, 2006

Related U.S. Application Data

(62) Division of application No. 10/848,737, filed on May 19, 2004, now Pat. No. 7,129,223.

(60) Provisional application No. 60/471,901, filed on May 19, 2003.

(51) Int. Cl.

*C07H 21/04* (2006.01)
*C07H 21/02* (2006.01)
*A01N 43/04* (2006.01)
*A61K 31/70* (2006.01)

(52) U.S. Cl. ....................... 536/24.5; 536/23.1; 514/44; 435/4; 435/6; 435/375

(58) Field of Classification Search ................ 536/23.1, 536/24.5; 514/44

See application file for complete search history.

(56) References Cited

U.S. PATENT DOCUMENTS

2001/0053519 A1 12/2001 Fodor et al.
2004/0265796 A1 12/2004 Briese et al.

FOREIGN PATENT DOCUMENTS

WO WO-2004/092383 10/2004

OTHER PUBLICATIONS

He et all., JAMA 290:2665-2666, 2003.
Paroo et al (Trends in Biotechnology 22:390-392, 2004).
Genbank Accession No. AY274119, "SARS Coronavirus Tor2, complete genome," version Ay274119.1, Apr. 14, 2003.
SARS-associated Coronavirus. Genomic Sequence Availability. [online] [retrived on Aug. 8, 2005], Retrieved from the Internet <URL: http://www.bcgsc.ca/bioinfo/SARS>.
Prentice et al (Journal of Virology 78:9977-9986, 2004, not prior art).

*Primary Examiner*—Jon E. Angell
*Assistant Examiner*—Dana Shin
(74) *Attorney, Agent, or Firm*—Saliwanchik, Lloyd & Saliwanchik

(57) ABSTRACT

The present invention relates to therapeutic agents useful for the treatment of Severe Acute Respiratory Syndrome (SARS) in humans. In particular, the present invention relates to RNA interference (RNAi) molecules useful for inhibiting the infection and replication of hSARS virus. Preferably, the RNAi molecules target the replicase region of the hSARS virus, or combinations of different sites of hSARS virus genes. The present invention further encompasses methods of using the RNAi molecules for preventing and/or treating SARS. Vaccines and kits comprising therapeutically effective amounts of the RNAi molecules are also encompassed.

3 Claims, 7 Drawing Sheets

Figures 1A, 1B:
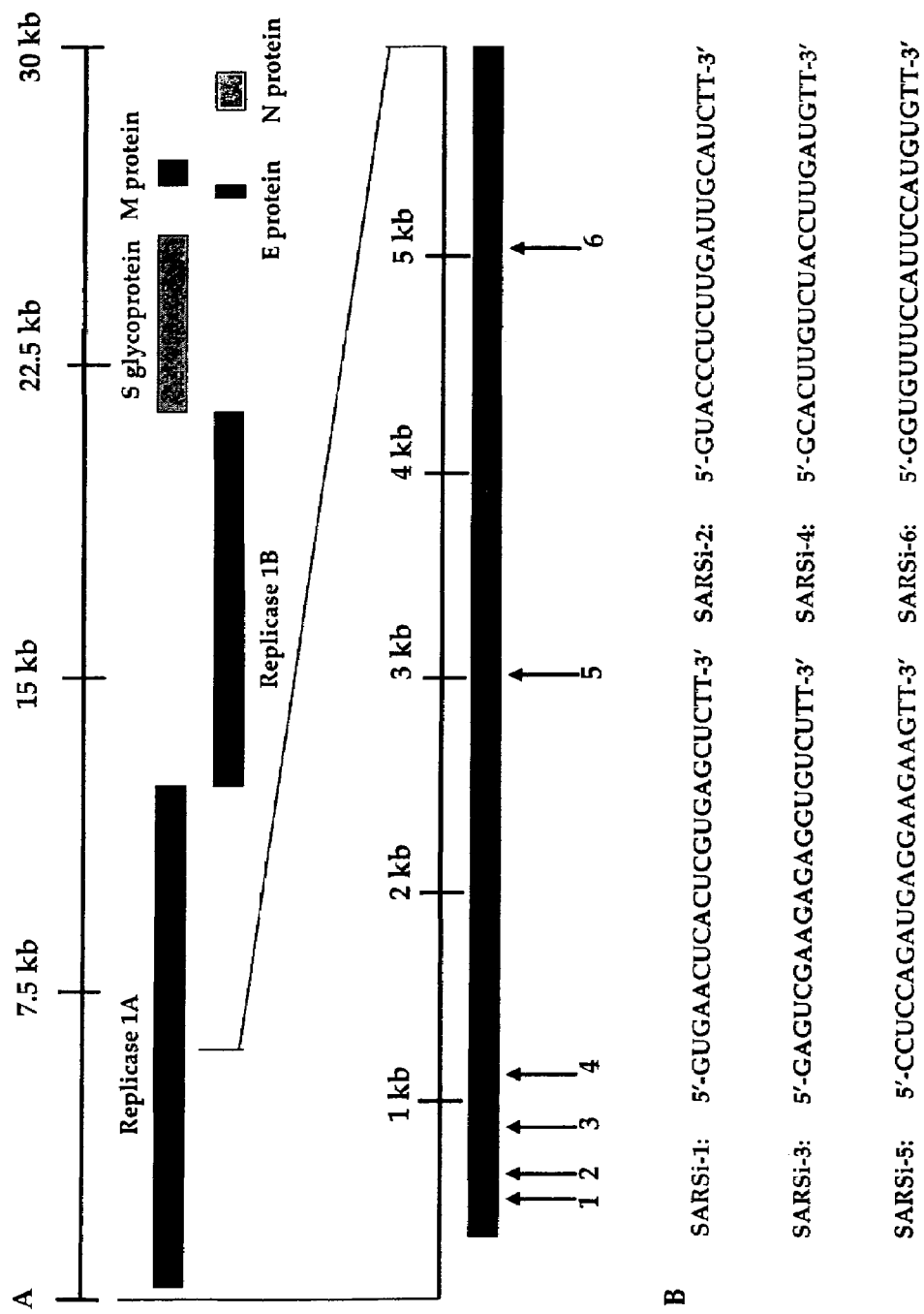

| SARSi-7: | 5'-CACUGAUUCCGUUCGAGAUCTT-3' |
| SARSi-8: | 5'-CGUUCGGAAGAAACAGGUACTT-3' |
| SARSi-9: | 5'-CAAGCCUCUUCUCGCUCCUCTT-3' |
| SARSi-10: | 5'-GUGGCUUAGCUACUUCGUUGTT-3' |
| SARSi-11: | 5'-UGCUUGCUGCUGUCUACAGTT-3' |

FIG. 5

INHIBITION OF SARS-ASSOCIATED CORONAVIRUS (SCOV) INFECTION AND REPLICATION BY RNA INTERFERENCE

This application is a division of U.S. patent application Ser. No. 10/848,737, filed May 19, 2004, now U.S. Pat. No. 7,129,223, issued Oct. 31, 2006; which claims the benefit of U.S. provisional application No. 60/471,901, filed May 19, 2003, both of which are incorporated herein by reference in their entireties.

1. INTRODUCTION

The present invention relates to therapeutic agents useful for the treatment of Severe Acute Respiratory Syndrome (SARS) in humans. The etiologic agent of SARS is a human RNA virus known as the hSARS virus. The hSARS virus is identified to be morphologically and phylogenetically similar to known members of Coronaviridae. The present invention relates to nucleic acid molecules comprising a nucleotide sequence which was designed based on portions of the genomic sequences of the different strains of the hSARS virus and their use as therapeutic agents in therapeutic methods. Specifically, the present invention relates to gene therapy, or the use of RNA interference (RNAi) molecules such as double-stranded RNA (dsRNA) or small interference RNA (siRNA) as therapeutic agents for the treatment of SARS in humans. Preferably, the RNAi molecules target the replicase region of the hSARS virus.

2. BACKGROUND OF THE INVENTION

Recently, there has been an outbreak of atypical pneumonia in Guangdong province in mainland China. Between November 2002 and March 2003, there were 792 reported cases with 31 fatalities (WHO. Severe Acute Respiratory Syndrome (SARS) *Weekly Epidemiol Rec.* 2003; 78: 86). In response to this crisis, the Hospital Authority in Hong Kong has increased the surveillance on patients with severe atypical pneumonia. In the course of this investigation, a number of clusters of health care workers with the disease were identified. In addition, there were clusters of pneumonia incidents among persons in close contact with those infected. The disease was unusual in its severity and its progression in spite of the antibiotic treatment typical for the bacterial pathogens that are known to be commonly associated with atypical pneumonia. The disease was given the acronym Severe Acute Respiratory Syndrome ("SARS").

A novel coronavirus associated with SARS (herein interchangeably referred to "SCoV", "CoV" or "hSARS" virus) has been identified as the etiologic agent of SARS (Ksiazek, T G, et al. A Novel Coronavirus Associated with Severe Acute Respiratory Syndrome. *N. Engl. J. Med.* 2003; published online (10.1056/NEJMMoa030781); Marra, M A, et al. The Genome Sequence of the SARS-Associated Coronavirus. *Science* 2003; published online (10.1126/science.1085953); Peiris, J S, et al. Coronavirus as a possible cause of severe acute respiratory syndrome. *Lancet* 2003; 361: 1319-1325; Drosten, C, et al. Identification of a Novel Coronavirus in Patients with Severe Acute Respiratory Syndrome. *N Engl J Med.* 2003; published online (10.1056/NEJMoa030747); and Rota, P A, et al. Characterization of a Novel Coronavirus Associated with Severe Acute Respiratory Syndrome. *Science* 2003; (10.1126/science.1085952)). The complete genome sequences of coronavirus strains isolated from different patients in various geographic locations were reported recently (Marra et al., supra.; Rota et al., supra.; and U.S. patent application Ser. Nos. 60/464,886, filed Apr. 23, 2003, and 10/808,121 filed Mar. 24, 2004; each of which is incorporated herein by reference in its entirety). The isolated virus is an enveloped, single-stranded RNA virus of positive polarity which belongs to the order, Nidovirales, of the family, Coronaviridae. The total genome of the SARS coronavirus is 29,727 nucleotides in length (see, for example, Genbank NCBI Accession Nos: AY274119, AY304495 and AY278491). This is the largest genome yet found in any of the known RNA viruses. The genome organization of the hSARS virus is similar to that of other coronaviruses. It encodes for at least 5 gene products, i.e., replicase, spike glycoprotein (S), membrane protein (M), envelope protein (E) and nucleocapsid protein (N), with eleven possible open reading frames (see FIGS. 1A and 4A). The exact numbers of gene products are not clear yet. Currently, there is no known effective treatment for SARS. Accordingly, drug development for the treatment of SARS is urgently needed. The inventors have formulated RNAi molecules useful for inhibiting the infection and replication of the hSARS virus. This offers the possibility of developing a new anti-viral therapy for SARS.

3. SUMMARY OF INVENTION

The present invention is based upon the inventor's use of gene therapy such as RNA interference (RNAi) molecules to inhibit coronavirus infection and replication. In particular, the invention relates to the use of small interfering RNA (siRNA) or double-stranded RNA (dsRNA) as therapeutic agents for the treatment of Severe Acute Respiratory Syndrome (SARS) in humans. The invention encompasses RNAi molecules that target different sites of the genome of the hSARS virus and inhibit infection and replication of the hSARS virus. Specifically, the invention encompasses siRNAs that target different sites of the replicase region of the hSARS virus and are useful for the treatment of SARS in humans. The present invention also encompasses small hairpin RNA (shRNA) containing plasmids under the control of a promoter useful for the treatment of SARS.

In certain embodiments, the invention relates to nucleic acid molecules comprising a portion of the genomic sequence of the hSARS virus. In preferred embodiments, the invention relates to nucleic acid molecules isolated from a replicase region of the genomic sequence of the hSARS virus. In certain other embodiments, the invention relates to nucleic acid molecules isolated from the spike glycoprotein (S) region, the membrane protein (M) region, the envelope protein (E) region, and the nucleocapsid protein (N) region of the hSARS viral genome.

In a specific embodiment, the nucleic acid molecules encode a polypeptide comprising a portion of the hSARS virus. Preferably, the nucleic acid molecules encode a polypeptide, or a portion thereof, comprising the replicase region of the hSARS virus.

In a specific embodiment, the invention relates to nucleic acid molecules encoding a polypeptide comprising a portion of the genomic sequence of the replicase region of the hSARS virus, or a portion thereof. Preferably, the replicase region of the hSARS virus is one that is described in FIG. 1 and Section 5, infra. In a preferred embodiment, the nucleic acid molecule comprises the nucleotide sequence of SEQ ID NO:1, 2, 3, 4, 5 or 6. In a specific embodiment, the present invention provides isolated nucleic acid molecules comprising or, alternatively, consisting of the nucleotide sequence of SEQ ID NO:1, a complement thereof or a portion thereof, preferably at least 5, 10, 15, 20, or more contiguous nucleotides of the nucleotide sequence of SEQ ID NO:1, or a complement thereof. In another specific embodiment, the present invention provides isolated nucleic acid molecules comprising or, alternatively, consisting of the nucleotide sequence of SEQ ID NO:2, a complement thereof or a portion thereof, preferably at least 5, 10, 15, 20, or more contiguous nucleotides of the nucleotide sequence of SEQ ID NO:2, or a complement thereof. In yet another specific embodiment, the present invention provides isolated nucleic acid molecules comprising or, alternatively, consisting of the nucleotide sequence of SEQ ID NO:3, a complement thereof or a portion thereof, preferably at least 5, 10, 15, 20, or more contiguous nucleotides of the nucleotide sequence of SEQ ID NO:3, or a complement thereof. In yet another specific embodiment, the present invention provides isolated nucleic acid molecules comprising or, alternatively, consisting of the nucleotide sequence of SEQ ID NO:4, a complement thereof or a portion thereof, preferably at least 5, 10, 15, 20, or more contiguous nucleotides of the nucleotide sequence of SEQ ID NO:4, or a complement thereof. In yet another specific embodiment, the present invention provides isolated nucleic acid molecules comprising or, alternatively, consisting of the nucleotide sequence of SEQ ID NO:5, a complement thereof or a portion thereof, preferably at least 5, 10, 15, 20, or more contiguous nucleotides of the nucleotide sequence of SEQ ID NO:5, or a complement thereof. In yet another specific embodiment, the present invention provides isolated nucleic acid molecules comprising or, alternatively, consisting of the nucleotide sequence of SEQ ID NO:6, a complement thereof or a portion thereof, preferably at least 5, 10, 15, 20, or more contiguous nucleotides of the nucleotide sequence of SEQ ID NO:6, or a complement thereof.

Figures 4A, 4B:
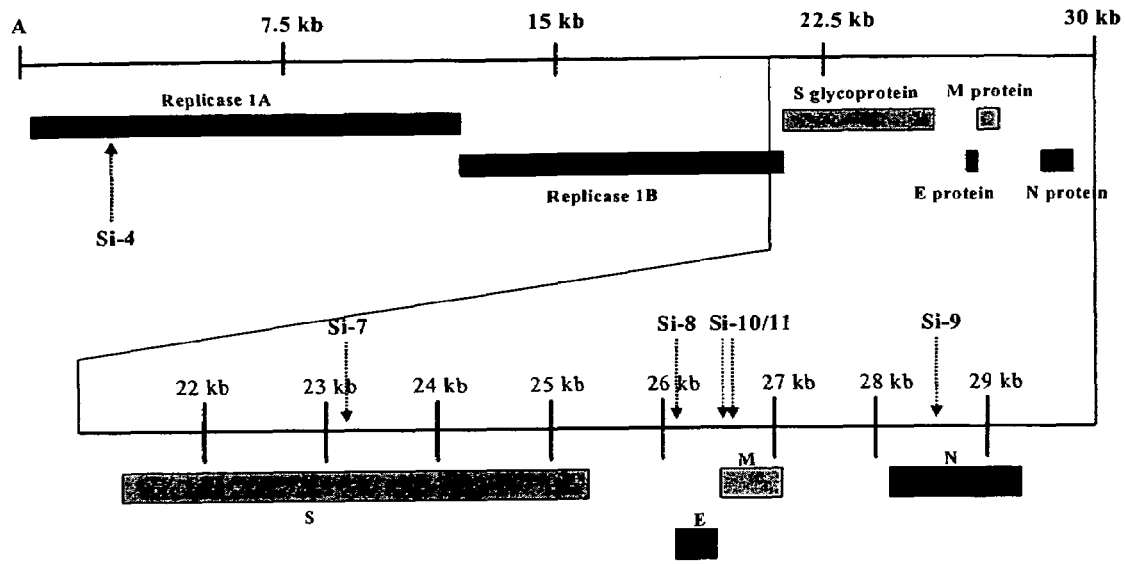

In yet another embodiment, the invention relates to nucleic acid molecules encoding a polypeptide comprising a portion of the genomic sequence of the spike glycoprotein (S) region, membrane protein (M) region, envelope protein (E) region, and/or nucleocapsid protein (N) region of the hSARS virus as described in FIG. 4A and Section 5, infra. In preferred embodiments, the nucleic acid molecule comprises the nucleotide sequence of SEQ ID NO:7, 8, 9, 10 or 11. In a specific embodiment, the present invention provides isolated nucleic acid molecules comprising or, alternatively, consisting of the nucleotide sequence of SEQ ID NO:7, a complement thereof or a portion thereof, preferably at least 5, 10, 15, 20, or more contiguous nucleotides of the nucleotide sequence of SEQ ID NO:7, or a complement thereof. In another specific embodiment, the present invention provides isolated nucleic acid molecules comprising or, alternatively, consisting of the nucleotide sequence of SEQ ID NO:8, a complement thereof or a portion thereof, preferably at least 5, 10, 15, 20, or more contiguous nucleotides of the nucleotide sequence of SEQ ID NO:8, or a complement thereof. In yet another specific embodiment, the present invention provides isolated nucleic acid molecules comprising or, alternatively, consisting of the nucleotide sequence of SEQ ID NO:9, a complement thereof or a portion thereof, preferably at least 5, 10, 15, 20, or more contiguous nucleotides of the nucleotide sequence of SEQ ID NO:9, or a complement thereof. In yet another specific embodiment, the present invention provides isolated nucleic acid molecules comprising or, alternatively, consisting of the nucleotide sequence of SEQ ID NO:10, a complement thereof or a portion thereof, preferably at least 5, 10, 15, 20, or more contiguous nucleotides of the nucleotide sequence of SEQ ID NO:10, or a complement thereof. In yet another specific embodiment, the present invention provides isolated nucleic acid molecules comprising or, alternatively, consisting of the nucleotide sequence of SEQ ID NO:11, a complement thereof or a portion thereof, preferably at least 5, 10, 15, 20, or more contiguous nucleotides of the nucleotide sequence of SEQ ID NO:11, or a complement thereof. Methods of RNA interference are also provided.

Furthermore, in another specific embodiment, the invention provides nucleic acid molecules which hybridize under stringent conditions, as defined herein, to a nucleic acid molecule having the sequence of SEQ ID NO:1, 2, 3, 4, 5, 6, 7, 8, 9, 10 or 11, or a fragment thereof, or a complement thereof. In one embodiment, the invention provides an isolated nucleic acid molecule which is antisense to the coding strand of a nucleic acid molecule of the invention.

In a specific embodiment, the invention provides isolated polypeptides or proteins that are encoded by a nucleic acid molecule comprising or, alternatively consisting of a nucleotide sequence that is at least 5, 10, 15, 20, or more contiguous nucleotides of the nucleotide sequence of SEQ ID NO:1, 2, 3, 4, 5, 6, 7, 8, 9, 10 or 11, or a complement thereof.

The invention further provides antibodies that specifically bind a polypeptide of the invention encoded by the nucleotide sequence of SEQ ID NO:1, 2, 3, 4, 5, 6, 7, 8, 9, 10 or 11, or a fragment thereof, or encoded by a nucleic acid comprising a nucleotide sequence that hybridizes under stringent conditions to the nucleotide sequence of SEQ ID NO:1, 2, 3, 4, 5, 6, 7, 8, 9, 10 or 11, having one or more biological activities of a polypeptide of the invention. Such antibodies include, but are not limited to polyclonal, monoclonal, bi-specific, multi-specific, human, humanized, chimeric antibodies, single chain antibodies, Fab fragments, F(ab')2 fragments, disulfide-linked Fvs, intrabodies and fragments containing either a VL or VH domain or even a complementary determining region (CDR) that specifically binds to a polypeptide of the invention.

The invention further relates to the use of the nucleic acid molecules for therapeutic methods. In a specific embodiment, the invention provides nucleic acid molecules which are suitable for administering into a subject in need thereof. In a preferred embodiment, the nucleic acid molecules comprise the nucleotide sequence of SEQ ID NO:1, 2, 3, 4, 5, 6, 7, 8, 9, 10 or 11, or a complement thereof, or at least a portion of the nucleotide sequence thereof. In one embodiment, the nucleic acid molecules are directly delivered into a host genome. In another embodiment, the nucleic acid molecules are encapsulated into liposomes. In yet another embodiment, the nucleic acid molecules are delivered using a vector system such as adenovirus, adeno-associated virus (AAV), or retrovirus.

In one embodiment, the invention provides methods for detecting the presence, activity or expression of the hSARS virus of the invention in a biological material, such as cells, blood, saliva, urine, nasopharyngeal aspirates, feces, and so forth. The increased or decreased activity or expression of the hSARS virus in a sample relative to a control sample can be determined by contacting the biological material with an agent which can detect directly or indirectly the presence, activity or expression of the hSARS virus. In a specific embodiment, the detecting agents are the antibodies or nucleic acid molecules of the present invention. Antibodies of the invention may also be used to treat SARS.

In another embodiment, the invention provides vaccine preparations, comprising the nucleic acid molecules of the present invention, including free and encapsulated forms of said nucleic acid molecule, or subunits of the nucleic acid molecule. In another embodiment, the invention provides vaccine preparations comprising one or more polypeptides of the invention encoded by the nucleotide sequence of SEQ ID NO:1, 2, 3, 4, 5, 6, 7, 8, 9, 10 or 11, or a fragment thereof. Furthermore, the present invention provides methods for treating, ameliorating, managing or preventing SARS by administering the vaccine preparations, antibodies or other anti-viral agents of the present invention alone or in combination with adjuvants, or other pharmaceutically acceptable excipients.

In another aspect, the present invention provides pharmaceutical compositions comprising anti-viral agents of the present invention and a pharmaceutically acceptable carrier. In a specific embodiment, the anti-viral agent of the invention is a nucleic acid molecule or the polypeptide encoded by the nucleic acid molecule of the invention, or the antibodies of the invention that immunospecifically binds hSARS virus or any hSARS epitope. In another specific embodiment, the anti-viral agent is a nucleic acid molecule which hybridizes genome or other RNA species of the hSARS virus under physiological condition. In another specific embodiment, the anti-viral agent is a polypeptide or protein of the present invention or nucleic acid molecule of the invention. The invention also provides kits containing a pharmaceutical composition of the present invention.

3.1 Definitions

The term "an antibody or an antibody fragment that immunospecifically binds a polypeptide of the invention" as used herein refers to an antibody or a fragment thereof that immunospecifically binds to the polypeptide encoded by the nucleotide sequence of SEQ ID NO:1, 2, 3, 4, 5, 6, 7, 8, 9, 10 or 11, or a fragment thereof, and does not non-specifically bind to other polypeptides. An antibody or a fragment thereof that immunospecifically binds to the polypeptide of the invention may cross-react with other antigens. Preferably, an antibody or a fragment thereof that immunospecifically binds to a polypeptide of the invention does not cross-react with other antigens. An antibody or a fragment thereof that immunospecifically binds to the polypeptide of the invention, can be identified by, for example, immunoassays or other techniques known to those skilled in the art.

An "isolated" or "purified" peptide or protein is substantially free of cellular material or other contaminating proteins from the cell or tissue source from which the protein is derived, or substantially free of chemical precursors or other chemicals when chemically synthesized. The language "substantially free of cellular material" includes preparations of a polypeptide/protein in which the polypeptide/protein is separated from cellular components of the cells from which it is isolated or recombinantly produced. Thus, a polypeptide/protein that is substantially free of cellular material includes preparations of the polypeptide/protein having less than about 30%, 20%, 10%, 5%, 2.5%, or 1%, (by dry weight) of contaminating protein. When the polypeptide/protein is recombinantly produced, it is also preferably substantially free of culture medium, i.e., culture medium represents less than about 20%, 10%, or 5% of the volume of the protein preparation. When polypeptide/protein is produced by chemical synthesis, it is preferably substantially free of chemical precursors or other chemicals, i.e., it is separated from chemical precursors or other chemicals which are involved in the synthesis of the protein. Accordingly, such preparations of the polypeptide/protein have less than about 30%, 20%, 10%, 5% (by dry weight) of chemical precursors or compounds other than polypeptide/protein fragment of interest. In a preferred embodiment of the present invention, polypeptides/proteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule or an RNA molecule, can be substantially free of other cellular material, or culture medium when produced by recombinant techniques, or substantially free of chemical precursors or other chemicals when chemically synthesized. In a preferred embodiment of the invention, nucleic acid molecules encoding polypeptides/proteins of the invention are isolated or purified. The term "isolated" nucleic acid molecule does not include a nucleic acid that is a member of a library that has not been purified away from other library clones containing other nucleic acid molecules.

The term "portion" or "fragment" as used herein refers to a fragment of a nucleic acid molecule containing at least about 5, 10, 15, 20, 25, 30, 35, 40, 45, 100, 150, 200, 250, 300, 350, 400, 450, 500, 550, 600, 650, 700, 750, 800, 850, 900, 950, 1000, 1050, 1100, 1150, 1200, 1250, 1300, 1350, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, or more contiguous nucleic acids in length of the relevant nucleic acid molecule and having at least one functional feature of the nucleic acid molecule (or the encoded protein has one functional feature of the protein encoded by the nucleic acid molecule); or a fragment of a protein or a polypeptide containing at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, 360, 400, 420, 440, 460, 480, 500, 520 or 540 amino acid residues in length of the relevant protein or polypeptide and having at least one functional feature of the protein or polypeptide.

The term "having a biological activity of the protein" or "having biological activities of the polypeptides of the invention" refers to the characteristics of the polypeptides or proteins having a common biological activity similar or identical structural domain and/or having sufficient amino acid identity to the polypeptide encoded by the nucleotide sequence of SEQ ID NO:1, 2, 3, 4, 5, 6, 7, 8, 9, 10 or 11. Such common biological activities of the polypeptides of the invention include antigenicity and immunogenicity.

The term "under stringent condition" refers to hybridization and washing conditions under which nucleotide sequences having at least 70%, at least 75%, at least 80%, at least 85%, at least 90%, or at least 95% identity to each other remain hybridized to each other. Such hybridization conditions are described in, for example but not limited to, Current Protocols in Molecular Biology, John Wiley & Sons, N.Y. (1989), 6.3.1-6.3.6.; Basic Methods in Molecular Biology, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes (e.g., about 5-30 min each) in 2×SSC, 0.5% SDS at room temperature. Another preferred, non-limiting example of stringent hybridization conditions is hybridization in 6×SSC at about 45° C. followed by one or more washes (e.g., about 5-30 min each) in 0.2× SSC, 0.1% SDS at about 45-65° C.

The term "variant" as used herein refers either to a naturally occurring genetic mutant of hSARS or a recombinantly prepared variation of hSARS. The term "variant" may also refers either to a naturally occurring variation of a given peptide or a recombinantly prepared variation of a given peptide or protein in which one or more amino acid residues have been modified by amino acid substitution, addition, or deletion.

4. DESCRIPTION OF THE FIGURES

FIG. 1A shows the open reading frame and functional domains of the hSARS virus. FIG. 1B shows the sense-strand sequences of six 21- and 22-mer siRNAs that target different sites of the replicase 1A region: SARSi-1 corresponds to the coronavirus nucleotide sequence 512 to 531 (SEQ ID NO:1); SARSi-2 corresponds to the coronavirus nucleotide sequence 586 to 604 (SEQ ID NO:2); SARSi-3 corresponds to the coronavirus nucleotide sequence 916 to 934 (SEQ ID NO:3); SARSi-4 corresponds to the coronavirus nucleotide sequence 1194 to 1213 (SEQ ID NO:4); SARSi-5 corresponds to the coronavirus nucleotide sequence 3028 to 3046 (SEQ ID NO:5); and SARSi-6 corresponds to the coronavirus nucleotide sequence 5024 to 5042 (SEQ ID NO:6).

Figure 2:
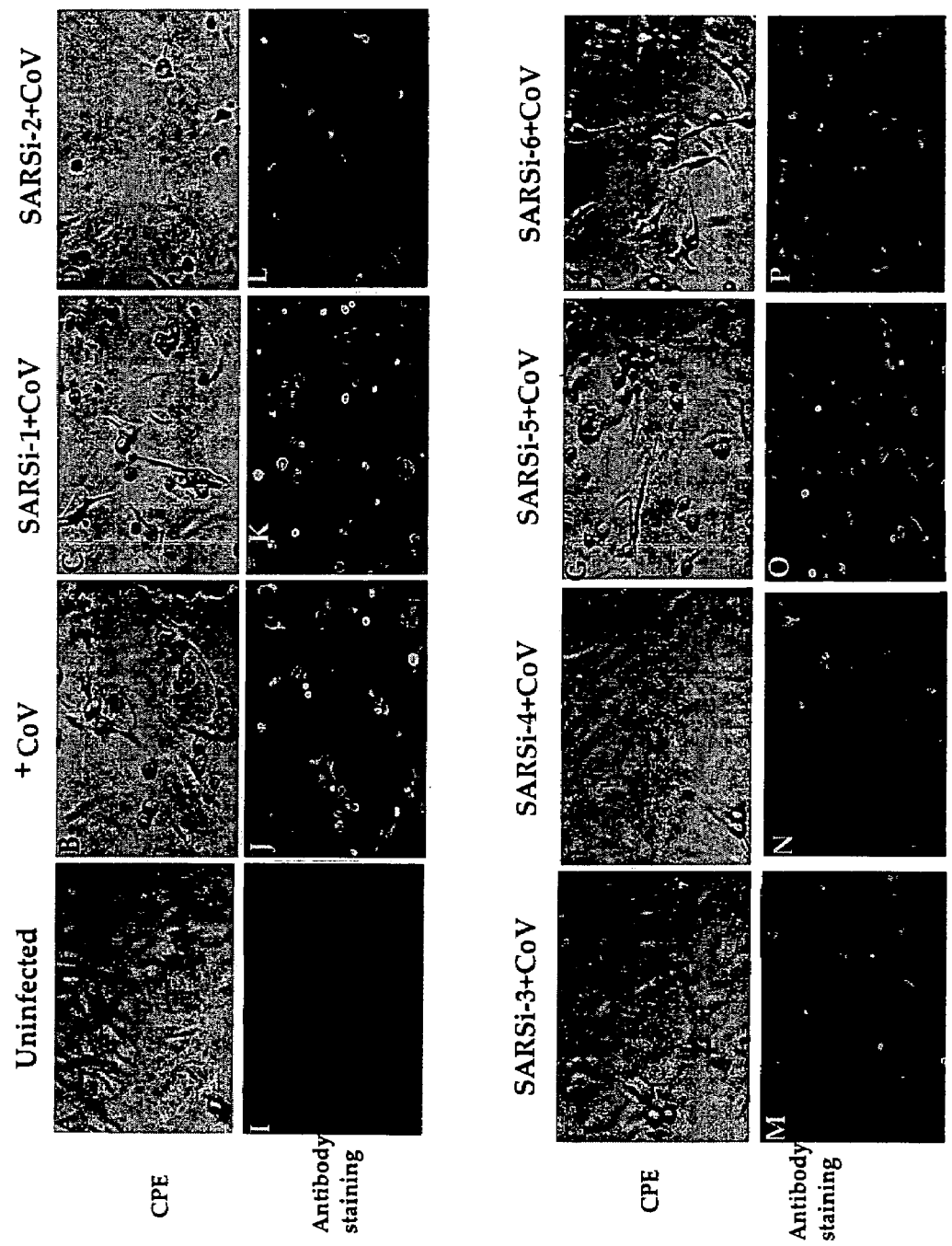

FIG. 2 shows the morphological changes with cytopathic effect (CPE) and immunostaining with antibody against coronavirus antigens of monkey kidney cells (FRhk-4 cells) infected with coronavirus (GZ50 strain). FRhk-4 cells were transfected with the siRNAs prior to infection with coronavirus. (A) shows the morphology and (I) shows antibody staining of uninfected cells. (B) shows the morphology and (J) shows antibody staining of SCoV-infected cells. (C)-(H) show the morphology and (K)-(P) show antibody staining of infected cells transfected with the siRNAs: SARSi-1, SARSi-2, SARSi-3, SARSi-4, SARSi-5, and SARSi-6, respectively.

Figure 3A:
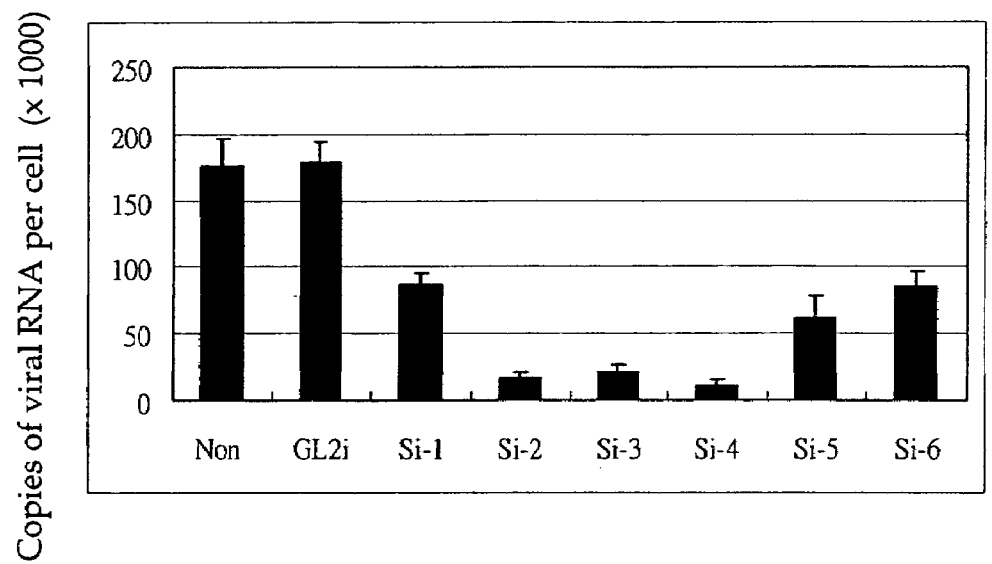
Figure 3B:
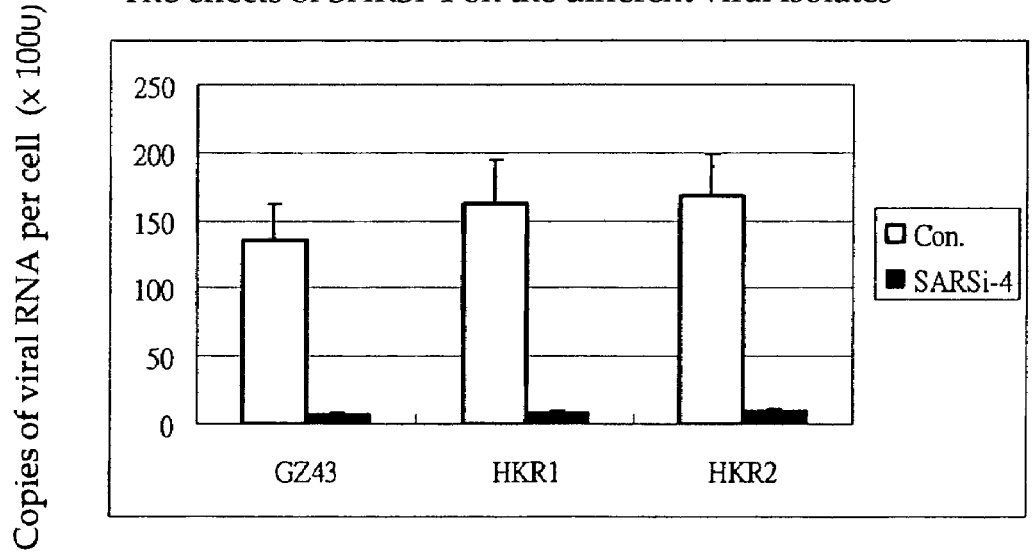

FIG. 3A shows the viral genomic RNA of infected cells with or without the treatment with siRNAs as determined by reverse transcription and polymerase chain reaction (RT-PCR). FIG. 3B shows the viral titer of cells infected with three (3) strains of coronavirus: GZ34 strain, HKR1 strain and HKR2 strain, respectively, with or without the treatment with SARSi-4.

FIG. 4A shows the physical map of SCoV. The targeting sites are shown by arrows. FIG. 4B shows the sense-strand sequences of five 21-, 22- and 23-mer siRNAs that target one site of the S glycoprotein region (SARSi-7, corresponding to the coronavirus nucleotide sequence 23165 to 23184; SEQ ID NO:7), one site of the E protein region (SARSi-8, corresponding to the coronavirus nucleotide sequence 26128 to 26148; SEQ ID NO:8), one site of the N protein region (SARSi-9, corresponding to the coronavirus nucleotide sequence 28663 to 28682; SEQ ID NO:9), and two sites of the M protein region (SARSi-10, corresponding to the coronavirus nucleotide sequence 26652 to 26671; SEQ ID NO:10, and SARSi-11, corresponding to the coronavirus nucleotide sequence 26575 to 26595; SEQ ID NO:11), respectively.

Figure 5:
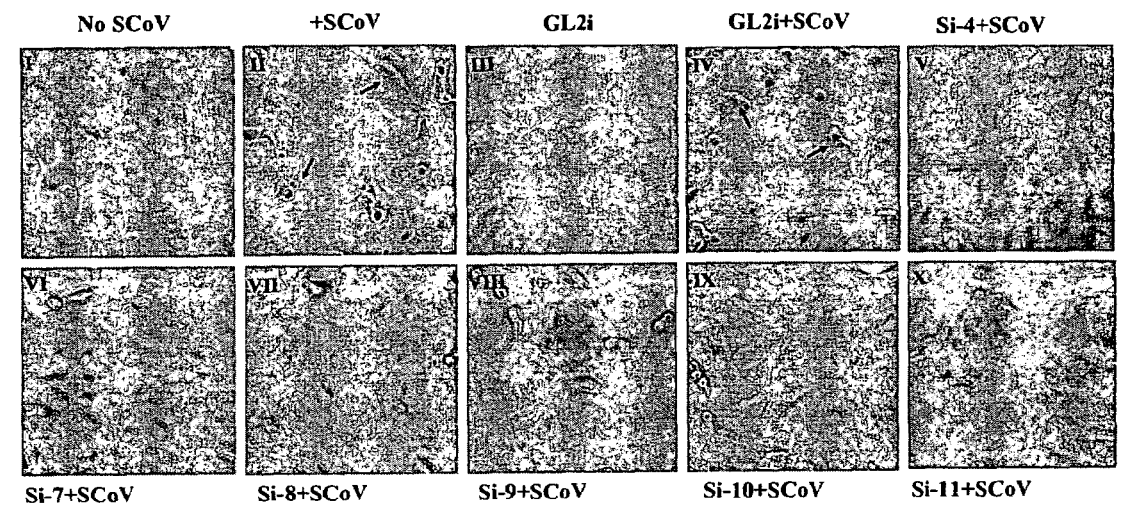

FIG. 5 shows the cytopathic effect ("CPE") on FRhk-4 cells. FRhk-4 cells were infected with SCoV at multiplicity of infection ("MOI") of 0.05 (II, IV to X) with (IV-X) or without siRNA (II). Non-infected cell (I) and GL2i-transfected cell without SCoV infection (III) served as controls. The photos were taken under phase-contrast microscopy (400×) with a light filter 24 hours post-infection. The arrows show the sick cells. "Si-" denotes "SARSi-".

Figure 6A:
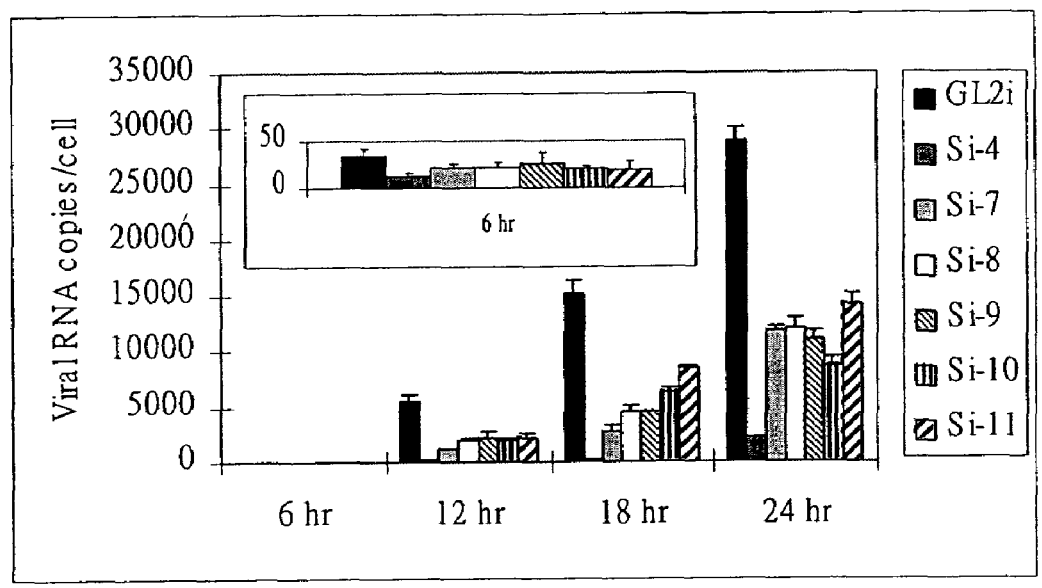
Figure 6B:
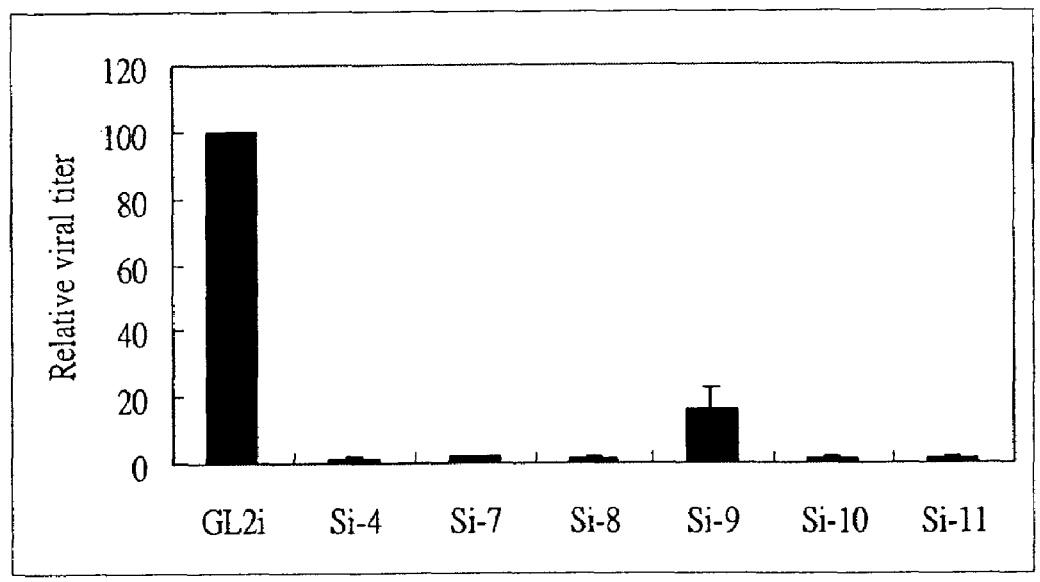
Figure 6C:
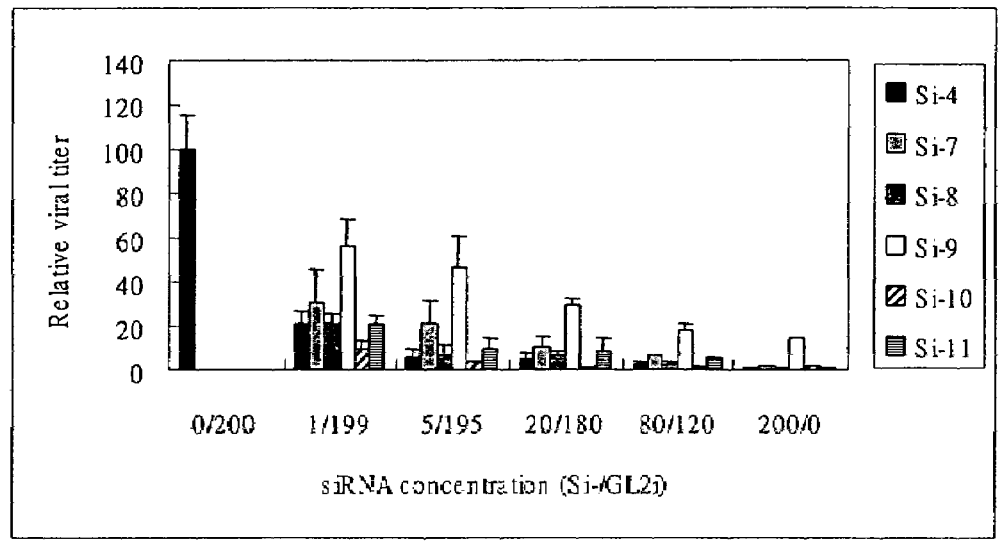
Figure 6D:
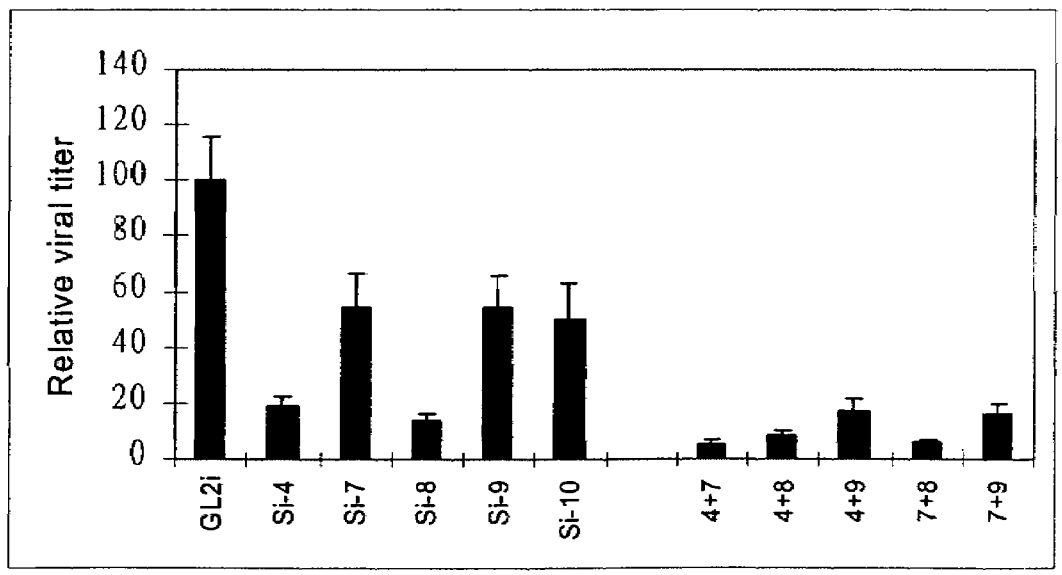

FIGS. 6A-6D show inhibition of SCoV replication and reproduction by siRNAs. FIG. 6A shows the levels of intracellular viral RNA copies at different time points after infection. FRhk-4 cells were transfected with siRNAs and infected with SCoV. The cellular RNA was isolated at different time points and quantitative RT-PCR was conducted. The experiments were performed in triplicate and repeated at least three times. The values (mean±standard error) represent the mean of three independent experiments. The viral genomic RNA copies per cell at 24 hours were calculated: GL2i, $1.69 \times 10^6 \pm 4.7 \times 10^3$; SARSi-4, $1.2 \times 10^5 \pm 5.5 \times 10^2$; SARSi-7, $2.5 \times 10^5 \pm 1.0 \times 10^5$; SARSi-8, $4.4 \times 10^5 \pm 1.0 \times 10^5$; SARSi-9, $3.8 \times 10^5 \pm 2.2 \times 10^5$; SARSi-10, $3.1 \times 10^5 \pm 1.2 \times 10^5$; and SARSi-11, $5.7 \times 10^5 \pm 1.5 \times 10^5$. FIG. 6B shows relative viral titers of SCoV in the culture media measured by back titration. The mean value of viral titers obtained from GL2i control was defined as 100. The relative viral titers of siRNAs targeted on SARS were: SARSi-4, 2.1±0.3; SARSi-7, 1.9±0.0.4; SARSi-8, 1.1±0.2; SARSi-9, 18.4±1.6; SARSi-10, 2±0.3; and SARSi-11, 2.2±0.4. FIG. 6C shows that siRNAs inhibited SCoV replication in a dose-dependent manner. FIG. 6D shows the effects of siRNAs used in combination. FRhk-4 cells were transfected with single siRNA (10 nM), or two combined siRNAs (5 nM each), and infected with SCoV (MOI of 0.05). At 24 hours post-infection the viral titers in the culture media were determined by back titration. The mean value of control (GL2i samples) was defined as 100. The values were as follows: GL2i, 100±12.8; Si-4, 16.7±3.8; Si-7, 54.2±12.1; Si-8, 13.5±2.8; Si-9, 54.8±10.8; Si-10, 50.2±13.2; Si-4/7, 5.6±1.3; Si-4/8, 8.3±1.9; Si-4/9, 17.3±4.2; Si-7/8, 5.8±1.2; and Si-7/10, 16.5±3.4.

5. DETAILED DESCRIPTION OF THE INVENTION

The present invention relates to RNA interference (RNAi) molecules useful for inhibiting coronavirus infection and replication. In particular, the invention relates to small interfering RNA (siRNA) and double-stranded RNA (dsRNA) useful for inhibiting coronavirus infection and replication. The present invention relates to nucleic acid molecules comprising portions of the genomic sequence of the hSARS virus, preferably the replicase region of the hSARS virus.

5.1 hSARS Virus

The present invention relates to the isolated hSARS virus that morphologically and phylogenetically relates to known *Coronaviruses*. In a specific embodiment, the virus comprises a nucleotide sequence of SEQ ID NO:1, 2, 3, 4, 5, 6, 7, 8, 9, 10 and/or 11. In a specific embodiment, the present invention provides isolated nucleic acid molecules of the hSARS virus, comprising, or, alternatively, consisting of the nucleotide sequence of SEQ ID NO:1, 2, 3, 4, 5, 6, 7, 8, 9, 10 and/or 11, a complement thereof or a portion thereof. In another specific embodiment, the invention provides isolated nucleic acid molecules which hybridize under stringent conditions, as defined herein, to a nucleic acid molecule having the sequence of SEQ ID NO:1, 2, 3, 4, 5, 6, 7, 8, 9, 10 or 11, or specific genes of known member of *Coronaviridae*, or a complement thereof.

In yet another specific embodiment, the invention provides isolated polypeptides or proteins that are encoded by a nucleic acid molecule comprising or, alternatively consisting of a nucleotide sequence that is at least 5, 10, 15, 20 or more contiguous nucleotides of the nucleotide sequence of SEQ ID NO:1, 2, 3, 4, 5, 6, 7, 8, 9, 10 or 11, or a complement thereof. The polypeptides or the proteins of the present invention preferably have one or more biological activities of the proteins encoded by the sequence of SEQ ID NO:1, 2, 3, 4, 5, 6, 7, 8, 9, 10 or 11, or the native viral proteins containing the amino acid sequences encoded by the sequence of SEQ ID NO:1, 2, 3, 4, 5, 6, 7, 8, 9, 10 and/or 11.

The invention further relates to the use of the sequence information of the isolated virus for and therapeutic methods.

In a specific embodiment, the present invention relates to a nucleic acid molecule that hybridizes any portion of the genome of various strains of the hSARS virus, including Genbank NCBI Accession Nos. AY304495, AY274119 and AY278491, under the stringent conditions. In a specific embodiment, the invention provides nucleic acid molecules which are suitable for use as primers consisting of or comprising the nucleotide sequence of SEQ ID NO:1, 2, 3, 4, 5, 6, 7, 8, 9, 10 and/or 11, or a complement thereof, or a portion thereof. In another specific embodiment, the invention provides nucleic acid molecules which are suitable for use as hybridization probes for the detection of nucleic acids encoding a polypeptide of the invention, consisting of or comprising the nucleotide sequence of SEQ ID NO:1, 2, 3, 4, 5, 6, 7, 8, 9, 10 or 11, a complement thereof, or a portion thereof. The invention further encompasses chimeric or recombinant viruses or viral proteins encoded by said nucleotide sequences.

The invention further provides antibodies that immunospecifically bind a polypeptide of the invention encoded by the nucleotide sequence of SEQ ID NO:1, 2, 3, 4, 5, 6, 7, 8, 9, 10 or 11, or a fragment thereof, or any hSARS epitope. Such antibodies include, but are not limited to polyclonal, monoclonal, bi-specific, multi-specific, human, humanized, chimeric antibodies, single chain antibodies, Fab fragments, F(ab')$_2$ fragments, disulfide-linked Fvs, intrabodies and fragments containing either a VL or VH domain or even a complementary determining region (CDR) that specifically binds to a polypeptide of the invention.

In one embodiment, the invention provides methods for detecting the presence, activity or expression of the hSARS virus of the invention in a biological material, such as cells, blood, saliva, urine, sputum, nasopharyngeal aspirates, and so forth. The presence of the hSARS virus in a sample can be determined by contacting the biological material with an agent which can detect directly or indirectly the presence of the hSARS virus. In a specific embodiment, the detection agents are the antibodies of the present invention. In another embodiment, the detection agent is a nucleic acid of the present invention.

In another embodiment, the invention provides vaccine preparations comprising one or more nucleic acid molecules comprising or consisting of the sequence of SEQ ID NO:1, 2, 3, 4, 5, 6, 7, 8, 9, 10 and/or 11, or a fragment thereof. In another embodiment, the invention provides vaccine preparations comprising one or more polypeptides of the invention encoded by a nucleotide sequence comprising or consisting of the nucleotide sequence of SEQ ID NO:1, 2, 3, 4, 5, 6, 7, 8, 9, 10 and/or 11, or a fragment thereof. The vaccine preparations of the present invention may further comprise pharmaceutically acceptable excipients, including adjuvants.

Furthermore, the present invention provides methods for treating, ameliorating, managing, or preventing SARS by administering the RNA interference (RNAi) molecules of the present invention alone or in combination with antivirals (e.g., amantadine, rimantadine, gancyclovir, acyclovir, ribavirin, penciclovir, oseltamivir, foscarnet zidovudine (AZT), didanosine (ddI), lamivudine (3TC), zalcitabine (ddC), stavudine (d4T), nevirapine, delavirdine, indinavir, ritonavir, vidarabine, nelfinavir, saquinavir, relenza, tamiflu, pleconaril, interferons, etc.), steroids and corticosteroids such as prednisone, cortisone, fluticasone and glucocorticoid, antibiotics, analgesics, bronchodialaters, or other treatments for respiratory and/or viral infections), thereby inhibiting infection and replication of the hSARS virus. In addition, the present invention provides methods for treating, ameliorating, managing, or preventing SARS by administering the vaccine preparations or antibodies of the present invention alone or in combination with antivirals.

Furthermore, the present invention provides pharmaceutical compositions comprising anti-viral agents of the present invention and a pharmaceutically acceptable carrier. The present invention also provides kits comprising pharmaceutical compositions of the present invention.

5.2 RNA Interference

The present invention specifically relates to the use of gene therapy to treat SARS in humans. In certain embodiments, gene therapy is conducted with the use of polynucleotide compounds, such as but not limited to antisense polynucleotides, ribozymes, RNA interference molecules, triple helix polynucleotides and the like, where the nucleotide sequence of such compounds are related to the nucleotide sequences of DNA and/or RNA of genes that are linked to the initiation mRNA transcription.

Antisense technology has been the most commonly described approach in protocols to achieve gene-specific interference. For antisense strategies, stoichiometric amounts of single-stranded nucleic acid complementary to the messenger RNA for the gene of interest are introduced into the cell. See U.S. Pat. No. 6,506,559, which is incorporated herein by reference in its entirety. Triple helical nucleic acid structures are also useful for engineered interference. This approach relies on the rare ability of certain nucleic acid populations to adopt a triple-stranded structure. Under physiological conditions, nucleic acids are virtually all single- or double-stranded, and rarely if ever form triple-stranded structures. It has been known for some time, however, that certain simple purine- or pyrimidine-rich sequences could form a triple-stranded molecule in vitro under extreme conditions of pH (i.e., in a test tube). Such structures are generally very transient under physiological conditions, so that simple delivery of unmodified nucleic acids designed to produce triple-strand structures does not yield interference.

In certain embodiments, an RNA interference (RNAi) molecule is used to decrease or inhibit expression of the nucleic acid against which the RNAi is directed. RNAi refers to the use of double-stranded RNA (dsRNA) or small interfering RNA (siRNA) to suppress the expression of a gene comprising a related nucleotide sequence. RNAi is also called post-transcriptional gene silencing (or PTGS). Since the only RNA molecules normally found in the cytoplasm of a cell are molecules of single-stranded mRNA, the cell has enzymes that recognize and cut dsRNA into fragments containing 21-25 base pairs (approximately two turns of a double helix and which are referred to as small interfering RNA or siRNA). The antisense strand of the fragment separates enough from the sense strand so that it hybridizes with the complementary sense sequence on a molecule of endogenous cellular mRNA. This hybridization triggers cutting of the mRNA in the double-stranded region, thus destroying its ability to be translated into a polypeptide. Introducing dsRNA corresponding to a particular gene thus knocks out the cell's own expression of that gene in particular tissues and/or at a chosen time. Thus, RNAi regulates gene expression via a ubiquitous mechanism by degradation of target mRNA in a sequence-specific manner. McManus et al., 2002, *Nat Rev Genet* 3:737-747. In mammalian cells, interfering RNA (RNAi) can be triggered by 21- to 23-nucleotide duplexes of siRNA. Lee et al., 2002, *Nat Biotechnol* 20: 500-505; Paul et al., 2002, *Nat Biotechnol.* 20:505-508; Miyagishi et al., 2002, *Nat Biotechnol.* 20:497-500; Paddison et al., 2002, *Genes Dev.* 16: 948-958. The expression of siRNA or short hairpin RNA (shRNA) driven by U6 promoter effectively mediates target mRNA degradation in mammalian cells. Synthetic siRNA duplexes and plasmid-derived siRNAs can inhibit HIV-1 infection and replication by specifically degrading HIV genomic RNA. McManus et al., *J. Immunol.* 169:5754-5760; Jacque et al., 2002, *Nature* 418:435-438; Novina et al., 2002, *Nat Med* 8:681-686. Also, siRNA targeting HCV genomic RNA inhibits HCV replication. Randall et al., 2003, *Proc Natl Acad Sci USA* 100:235-240; Wilson et al., 2003, *Proc Natl Acad Sci USA* 100: 2783-2788. Fas targeted by siRNA protects the liver from fulminant hepatitis and fibrosis. Song et al., 2003, *Nat Med* 9:347-351. However, the possibility that RNA interference might inhibit hSARS viral replication has not been known until the present invention.

Double-stranded (ds) RNA can be used to interfere with gene expression in many organisms including, but not limited to mammals. dsRNA is used as inhibitory RNA or RNAi of the function of a nucleic acid molecule of the invention to produce a phenotype that is the same as that of a null mutant of a nucleic acid molecule of the invention (Wianny & Zernicka-Goetz, 2000, *Nature Cell Biology* 2: 70-75).

Many methods have been developed to make siRNA, e.g., chemical synthesis or in vitro transcription. Once made, the siRNA can be introduced directly into a cell to mediate RNA interference (Elbashir et al., 2001, *Nature* 411: 494-498; Song, E, et al. RNA interference targeting Fas protects mice from fulminant hepatitis. *Nat. Med.* 2003; 9: 347-351; and Lewis, D L, et al. Efficient delivery of siRNA for inhibition of gene expression in postnatal mice. *Nat. Genet.* 2002; 32: 107-108). Alternatively, the siRNA can be encapsulated into liposomes to facilitate delivery into a cell (Sorensen, D R, et al. Gene silencing by systemic delivery of synthetic siRNAs in adult mice. *J Mol Biol.* 2003; 327: 761-766). The siRNAs can also be introduced into cells via transient transfection. See also U.S. patent application Nos. 60/265232 and 09/821832, and International Application No. PCT/US01/10188, directed to RNA sequence-specific mediators of RNA interference.

A number of expression vectors have also been developed to continually express siRNAs in transiently and stably transfected mammalian cells (Brummelkamp et al., 2002, *Science* 296: 550-553; Sui et al., 2002, *PNAS* 99(6): 5515-5520; Paul et al., 2002, *Nature Biotechnol.* 20: 505-508). Some of these vectors have been engineered to express small hairpin RNAs (shRNAs), which get processed in vivo into siRNA-like molecules capable of carrying out gene-specific silencing. In certain embodiments, an shRNA contains plasmid under the control of a promoter, preferably a U6 promoter (Paul, CP, et al. Effective expression of small interfering RNA in human cells. *Nat. Biotechnol.* 2002; 20: 505-508). Another type of siRNA expression vector encodes the sense and antisense siRNA strands under control of separate pol III promoters (Miyagishi and Taira, 2002, *Nature Biotechnol.* 20: 497-500). The siRNA strands from this vector, like the shRNAs of the other vectors, have 3' thymidine termination signals. The shRNA gene can be delivered via a suitable vector system, e.g., adenovirus, adeno-associated virus (AAV), or retrovirus (Xia, H, et al. siRNA-mediated gene silencing in vitro and in vivo. *Nat. Biotechnol.* 2002; 20: 1006-1010; and Barton, G M, et al. Retroviral delivery of small interfering RNA into primary cells. *Proc. Natl. Acad. Sci. USA* 2002; 99: 14943-14945). Silencing efficacy by both types of expression vectors is comparable to that induced by transiently transfecting siRNA.

The RNA may comprise one or more strands of polymerized ribonucleotide. It may include modifications to either the phosphate-sugar backbone or the nucleoside. For example, the phophodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. RNA may be produced enzymatically or by partial/total organic synthesis; any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition. The RNA molecule may be at least 10, 12, 15, 20, 21, 22, 23, 24, 25 or 30 nucleotides in length.

siRNAs of the present invention specifically target the region of SCoV viral RNA species encoding Replicase 1A, S glycoprotein, E protein, M protein and N protein, respectively (FIGS. 1A and 4A). The non-structural rep gene products play key roles in viral replication and gene transcription. The structure proteins play critical roles in viral entry (S), package (E, N), and secretion (M). It is particularly important to develop effective siRNAs targeting structure genes, because drugs used in combination with multiple targets usually exhibit enhanced antiviral effects and eliminate drug resistant mutations.

RNA containing a nucleotide sequences identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Deveeux, Sequence Analysis primer, Stockton Press, 1991, and references cited therein) and calculating the percent difference between the nucleotide sequences by, for example, the smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES, pH6.4, 1 mM EDTA, 50° C. or 70° C. hybridization for 12-16 hours; followed by washing). The length of the identical nucleotide sequences may be at least 10, 25, 50, 100, 200, 300 or 400 bases.

One hundred percent sequence identity between the RNA and the target gene is not required to practice the present invention. Thus, the invention has the advantage of being able to tolerate sequence variations that might be expected due to genetic mutation, strain polymorphism, or evolutionary divergence.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see also WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

RNA may be directly introduced into the cell (i.e., intracellularly); or introduced extracellularly into a cavity, interstitial space, into the circulation of an organism, introduced orally, or may be introduced by bathing an organism in a solution containing the RNA. Physical methods of introducing nucleic acids, for example, injection directly into the cell or extracellular injection into the organism, may also be used. Vascular or extravascular circulation, the blood or lymph system, and the cerebrospinal fluid are sites where the RNA may be introduced.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or other-wise increase inhibition of the target gene.

RNAi technology has been adapted for high throughput use in *C. elegans* (see, e.g., Kamath et al., 2003, *Nature* 421: 231-7, Ashrafi et al., 2003, *Nature* 421: 268-72, Taschl, 2003, *Nature* 421: 220-221). Briefly, DNA plasmids encoding a double-stranded RNA (dsRNA) of choice are inserted into *E. coli*. The nucleic acid encoding the dsRNA can be placed under the control of an inducible promoter such that expression in *E. coli* occurs only in the presence of the inducing molecule (e.g., IPTG). Nematodes at the latest larval stage are placed on a lawn of *E. coli* expressing the dsRNA and allowed to feed on the *E. coli*. The ingested bacteria release the dsRNA inside the nematode. As a result, the gene whose sequence corresponds to that of the dsRNA behaves as if the gene carries a loss-of-function mutation.

In the present invention, siRNAs may be combined with other anti-viral agents to increase its anti-SCoV efficacy. Furthermore, the siRNAs of the present invention that target different sites of the gene regions or different RNA species of SCoV, may be combined with one another.

Accordingly, the present invention provides methods of inhibiting hSARS infection, or replication in a cell by administering to the cell an effective amount of the nucleic acid molecule comprising or, alternatively consisting of the nucleotide sequence of SEQ ID NO:1, 2, 3, 4, 5, 6, 7, 8, 9, 10 and/or 11, or a complement thereof, or a portion thereof. Furthermore, the present invention provides methods of preventing, ameliorating, treating or managing SARS by administering to a subject in need thereof a therapeutically or prophylactically effective amount of the nucleic acid molecule comprising the nucleotide sequence of SEQ ID NO:1, 2, 3, 4, 5, 6, 7, 8, 9, 10 and/or 11, or a complement thereof, or a portion thereof.

5.3 Recombinant and Chimeric hSARS Viruses

The present invention encompasses recombinant or chimeric viruses encoded by viral vectors derived from the genome of hSARS virus or natural variants thereof. In a specific embodiment, the virus has a genome comprising the nucleotide sequence of SEQ ID NO:1, 2, 3, 4, 5, 6, 7, 8, 9, 10 and/or 11, or a portion thereof, or a variant thereof, due to one or more naturally occurred mutations or by recombinant DNA technology, including, but not limited to, point mutations, rearrangements, insertions, deletions etc., to the genomic sequence that may or may not result in a phenotypic change. In accordance with the present invention, a viral vector which is derived from the genome of the hSARS virus, is one that contains a nucleic acid sequence that encodes at least a part of one ORF of the hSARS virus. In a specific embodiment, the ORF comprises or consists of a nucleotide sequence of SEQ ID NO:1, 2, 3, 4, 5, 6, 7, 8, 9, 10 or 11, or a fragment thereof. In a specific embodiment, there are more than one ORF within the nucleotide sequence of the hSARS genome, or a fragment thereof. In accordance with the present invention these viral vectors may or may not include nucleic acids that are non-native to the viral genome.

In another specific embodiment, a chimeric virus of the invention is a recombinant hSARS virus which further comprises a heterologous nucleotide sequence. In accordance with the invention, a chimeric virus may be encoded by a nucleotide sequence in which heterologous nucleotide sequences have been added to the genome or in which endogenous or native nucleotide sequences have been replaced with heterologous nucleotide sequences.

According to the present invention, the chimeric viruses are encoded by the viral vectors of the invention which further comprise a heterologous nucleotide sequence. In accordance with the present invention a chimeric virus is encoded by a viral vector that may or may not include nucleic acids that are non-native to the viral genome. In accordance with the invention a chimeric virus is encoded by a viral vector to which heterologous nucleotide sequences have been added, inserted or substituted for native or non-native sequences. In accordance with the present invention, the chimeric virus may be encoded by nucleotide sequences derived from different strains or variants of hSARS virus. In particular, the chimeric virus is encoded by nucleotide sequences that encode antigenic polypeptides derived from different strains or variants of hSARS virus.

A chimeric virus may be of particular use for the generation of recombinant vaccines protecting against two or more viruses (Tao et al., *J. Virol.* 72: 2955-2961; Durbin et al., 2000, J. Virol. 74: 6821-6831; Skiadopoulos et al., 1998, J. Virol. 72: 1762-1768; Teng et al., 2000, J. Virol. 74: 9317-9321). For example, it can be envisaged that a virus vector derived from the hSARS virus expressing one or more proteins of variants of hSARS virus, or vice versa, will protect a subject vaccinated with such vector against infections by both the native hSARS and the variant. Attenuated and replication-defective viruses may be of use for vaccination purposes with live vaccines as has been suggested for other viruses. (See, PCT WO 02/057302, at pp. 6 and 23, incorporated by reference herein).

In accordance with the present invention the heterologous sequence to be incorporated into the viral vectors encoding the recombinant or chimeric viruses of the invention include sequences obtained or derived from different strains or variants of hSARS.

In certain embodiments, the chimeric or recombinant viruses of the invention are encoded by viral vectors derived from viral genomes wherein one or more sequences, intergenic regions, termini sequences, or portions or entire ORF have been substituted with a heterologous or non-native sequence. In certain embodiments of the invention, the chimeric viruses of the invention are encoded by viral vectors derived from viral genomes wherein one or more heterologous sequences have been inserted or added to the vector.

The selection of the viral vector may depend on the species of the subject that is to be treated or protected from a viral infection. If the subject is human, then an attenuated hSARS virus can be used to provide the antigenic sequences.

In accordance with the present invention, the viral vectors can be engineered to provide antigenic sequences which confer protection against infection by the hSARS and natural variants thereof. The viral vectors may be engineered to provide one, two, three or more antigenic sequences. In accordance with the present invention the antigenic sequences may be derived from the same virus, from different strains or variants of the same type of virus, or from different viruses.

The expression products and/or recombinant or chimeric virions obtained in accordance with the invention may advantageously be utilized in vaccine formulations. The expression products and chimeric virions of the present invention may be engineered to create vaccines against a broad range of pathogens, including viral and bacterial antigens, tumor antigens, allergen antigens, and auto antigens involved in autoimmune disorders. In particular, the chimeric virions of the present invention may be engineered to create vaccines for the protection of a subject from infections with hSARS virus and variants thereof.

In certain embodiments, the expression products and recombinant or chimeric virions of the present invention may be engineered to create vaccines against a broad range of pathogens, including viral antigens, tumor antigens and autoantigens involved in autoimmune disorders. One way to achieve this goal involves modifying existing hSARS genes to contain foreign sequences in their respective external domains. Where the heterologous sequences are epitopes or antigens of pathogens, these chimeric viruses may be used to induce a protective immune response against the disease agent from which these determinants are derived.

Thus, the present invention relates to the use of viral vectors and recombinant or chimeric viruses to formulate vaccines against a broad range of viruses and/or antigens. The present invention also encompasses recombinant viruses comprising a viral vector derived from the hSARS or variants thereof which contains sequences which result in a virus having a phenotype more suitable for use in vaccine formulations, e.g., attenuated phenotype or enhanced antigenicity.

The mutations and modifications can be in coding regions, in intergenic regions and in the leader and trailer sequences of the virus.

The invention provides a host cell comprising a nucleic acid or a vector according to the invention. Plasmid or viral vectors containing the polymerase components of hSARS virus are generated in prokaryotic cells for the expression of the components in relevant cell types (bacteria, insect cells, eukaryotic cells). Plasmid or viral vectors containing full-length or partial copies of the hSARS genome will be generated in prokaryotic cells for the expression of viral nucleic acids in-vitro or in-vivo. The latter vectors may contain other viral sequences for the generation of chimeric viruses or chimeric virus proteins, may lack parts of the viral genome for the generation of replication defective virus, and may contain mutations, deletions or insertions for the generation of attenuated viruses.

Infectious copies of hSARS (being wild type, attenuated, replication-defective or chimeric) can be produced upon co-expression of the polymerase components according to the state-of-the-art technologies described above.

In addition, the present invention provides eukaryotic cells, transiently or stably expressing one or more full-length or partial hSARS viral nucleic acids or proteins. Such cells can be made by transfection (proteins or nucleic acid vectors), infection (viral vectors) or transduction (viral vectors) and may be useful for complementation of mentioned wild type, attenuated, replication-defective or chimeric viruses.

Accordingly, the present invention further provides a host cell that is transfected or transduced with the nucleic acid molecules of the present invention or infected with the chimeric viruses of the present invention.

The viral vectors and chimeric viruses of the present invention may be used to modulate a subject's immune system by stimulating a humoral immune response, a cellular immune response or by stimulating tolerance to an antigen. As used herein, a subject means: humans, primates, horses, cows, sheep, pigs, goats, dogs, cats, avian species and rodents.

5.4 Formulation of Vaccines

In a preferred embodiment, the invention provides a proteinaceous molecule or hSARS virus specific viral protein or functional fragment thereof encoded by a nucleic acid according to the invention. Useful proteinaceous molecules are for example derived from any of the genes or genomic fragments derivable from the virus according to the invention, including envelop protein (E protein), integral membrane protein (M protein), spike protein (S protein), nucleocapsid protein (N protein), hemaglutinin esterase (HE protein), and RNA-dependent RNA polymerase. Such molecules, or antigenic fragments thereof, as provided herein, are for example useful in diagnostic methods or kits and in pharmaceutical compositions such as subunit vaccines. Particularly useful are polypeptides encoded by the nucleotide sequence of SEQ ID NO:1, 2, 3, 4, 5, 6, 7, 8, 9, 10 or 11, or antigenic fragments thereof for inclusion as antigen or subunit immunogen. Particularly useful are also those proteinaceous substances that are encoded by recombinant nucleic acid fragments of the hSARS genome, of course preferred are those that are within the preferred bounds and metes of ORFs, in particular, for eliciting hSARS specific antibody or T cell responses, whether in vivo (e.g., for protective or therapeutic purposes or for providing diagnostic antibodies) or in vitro (e.g., by phage display technology or another technique useful for generating synthetic antibodies).

The invention provides vaccine formulations for the prevention and treatment of infections with hSARS virus. In certain embodiments, the vaccine of the invention comprises recombinant and chimeric viruses of the hSARS virus, comprising a nucleotide sequence of SEQ ID NO:1, 2, 3, 4, 5, 6, 7, 8, 9, 10 and/or 11.

The vaccine of the present invention may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and *Corynebacterium parvum*.

In another aspect, the present invention also provides DNA vaccine formulations comprising nucleic acid molecules having the sequence of SEQ ID NO:1, 2, 3, 4, 5, 6, 7, 8, 9, 10 and/or 11, or a fragment thereof. In another specific embodiment, the DNA vaccine formulations of the present invention comprises a nucleic acid or fragment thereof encoding the antibodies which immunospecifically binds hSARS viruses. In DNA vaccine formulations, a vaccine DNA comprises a viral vector, such as that derived from the hSARS virus, bacterial plasmid, or other expression vector, bearing an insert comprising a nucleic acid molecule of the present invention operably linked to one or more control elements, thereby allowing expression of the vaccinating proteins encoded by said nucleic acid molecule in a vaccinated subject. Such vectors can be prepared by recombinant DNA technology as recombinant or chimeric viral vectors carrying a nucleic acid molecule of the present invention (see also Section 5, supra).

Various heterologous vectors are described for DNA vaccinations against viral infections. For example, the vectors described in the following references may be used to express hSARS sequences instead of the sequences of the viruses or other pathogens described; in particular, vectors described for hepatitis B virus (Michel, M. L. et al., 1995, DAN-mediated immunization to the hepatitis B surface antigen in mice: Aspects of the humoral response mimic hepatitis B viral infection in humans, *Proc. Natl. Acta. Sci. USA* 92: 5307-5311; Davis, H. L. et al., 1993, DNA-based immunization induces continuous seretion of hepatitis B surface antigen and high levels of circulating antibody, *Human Molec. Genetics* 2: 1847-1851), HIV virus (Wang, B. et al., 1993, Gene inoculation generates immune responses against human immunodeficiency virus type 1, *Proc. Natl. Acad. Sci. USA* 90: 4156-4160; Lu, S. et al., 1996, Simian immunodeficiency virus DNA vaccine trial in macques, *J. Virol.* 70: 3978-3991; Letvin, N. L. et al., 1997, Potent, protective anti-HIV immune responses generated by bimodal HIV envelope DNA plus protein vaccination, *Proc Natl Acad Sci USA*. 94(17): 9378-83), and influenza viruses (Robinson, H L et al., 1993, Protection against a lethal influenza virus challenge by immunization with a haemagglutinin-expressing plasmid DNA, *Vaccine* 11: 957-960; Ulmer, J. B. et al., Heterologous protection against influenza by injection of DNA encoding a viral protein, *Science* 259: 1745-1749), as well as bacterial infections, such as tuberculosis (Tascon, R. E. et al., 1996, Vaccination against tuberculosis by DNA injection, *Nature Med.* 2: 888-892; Huygen, K. et al., 1996, Immunogenicity and protective efficacy of a tuberculosis DNA vaccine, *Nature Med,* 2: 893-898), and parasitic infection, such as malaria (Sedegah, M., 1994, Protection against malaria by immunization with plasmid DNA encoding circumsporozoite protein, *Proc. Natl. Acad. Sci. USA* 91: 9866-9870; Doolan, D. L. et al., 1996, Circumventing genetic restriction of protection against malaria with multigene DNA immunization: CD8+T cell-interferon δ, and nitric oxide-dependent immunity, *J. Exper. Med.,* 1183: 1739-1746).

Many methods may be used to introduce the vaccine formulations described above. These include, but are not limited to, oral, intradermal, intramuscular, intraperitoneal, intravenous, subcutaneous, and intranasal routes. Alternatively, it may be preferable to introduce the chimeric virus vaccine formulation via the natural route of infection of the pathogen for which the vaccine is designed. The DNA vaccines of the present invention may be administered in saline solutions by injections into muscle or skin using a syringe and needle (Wolff J. A. et al., 1990, Direct gene transfer into mouse muscle in vivo, *Science* 247: 1465-1468; Raz, E., 1994, Intradermal gene immunization: The possible role of DNA uptake in the induction of cellular immunity to viruses, *Proc. Natl. Acd. Sci. USA* 91: 9519-9523). Another way to administer DNA vaccines is called "gene gun" method, whereby microscopic gold beads coated with the DNA molecules of interest is fired into the cells (Tang, D. et al., 1992, Genetic immunization is a simple method for eliciting an immune response, *Nature* 356: 152-154). For general reviews of the methods for DNA vaccines, see Robinson, H. L., 1999, DNA vaccines: basic mechanism and immune responses (Review), *Int. J. Mol. Med.* 4(5): 549-555; Barber, B., 1997, Introduction: Emerging vaccine strategies, *Seminars in Immunology* 9(5): 269-270; and Robinson, H. L. et al., 1997, DNA vaccines, *Seminars in Immunology* 9(5): 271-283.

5.5 Adjuvants and Carrier Molecules hSARS-associated antigens are administered with one or more adjuvants. In one embodiment, the hSARS-associated antigen is administered together with a mineral salt adjuvants or mineral salt gel adjuvant. Such mineral salt and mineral salt gel adjuvants include, but are not limited to, aluminum hydroxide (ALHYDROGEL, REHYDRAGEL), aluminum phosphate gel, aluminum hydroxyphosphate (ADJU-PHOS), and calcium phosphate.

In another embodiment, hSARS-associated antigen is administered with an immunostimulatory adjuvant. Such class of adjuvants, include, but are not limited to, cytokines (e.g., interleukin-2, interleukin-7, interleukin-12, granulocyte-macrophage colony stimulating factor (GM-CSF), interfereon-γ interleukin-1β (IL-1β), and IL-1β peptide or Sclavo Peptide), cytokine-containing liposomes, triterpenoid glycosides or saponins (e.g., QuilA and QS-21, also sold under the trademark STIMULON, ISCOPREP), Muramyl Dipeptide (MDP) derivatives, such as N-acetyl-muramyl-L-threonyl-D-isoglutamine (Threonyl-MDP, sold under the trademark TERMURTIDE), GMDP, N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxy phosphoryloxy)-ethylamine, muramyl tripeptide phosphatidylethanolamine (MTP-PE), unmethylated CpG dinucleotides and oligonucleotides, such as bacterial DNA and fragments thereof, LPS, monophosphoryl Lipid A (3D-MLA sold under the trademark MPL), and polyphosphazenes.

In another embodiment, the adjuvant used is a particular adjuvant, including, but not limited to, emulsions, e.g., Freund's Complete Adjuvant, Freund's Incomplete Adjuvant, squalene or squalane oil-in-water adjuvant formulations, such as SAF and MF59, e.g., prepared with block-copolymers, such as L-121 (polyoxypropylene/polyoxyetheylene) sold under the trademark PLURONIC L-121, Liposomes, Virosomes, cochleates, and immune stimulating complex, which is sold under the trademark ISCOM.

In another embodiment, a microparticular adjuvant is used., Microparticulare adjuvants include, but are not limited to biodegradable and biocompatible polyesters, homo- and copolymers of lactic acid (PLA) and glycolic acid (PGA), poly(lactide-co-glycolides) (PLGA) microparticles, polymers that self-associate into particulates (poloxamer particles), soluble polymers (polyphosphazenes), and virus-like particles (VLPs) such as recombinant protein particulates, e.g., hepatitis B surface antigen (HbsAg).

Yet another class of adjuvants that may be used include mucosal adjuvants, including but not limited to heat-labile enterotoxin from *Escherichia coli* (LT), cholera holotoxin (CT) and cholera Toxin B Subunit (CTB) from *Vibrio cholerae*, mutant toxins (e.g., LTK63 and LTR72), microparticles, and polymerized liposomes.

In other embodiments, any of the above classes of adjuvants may be used in combination with each other or with other adjuvants. For example, non-limiting examples of combination adjuvant preparations that can be used to administer the hSARS-associated antigens of the invention include liposomes containing immunostimulatory protein, cytokines, or T-cell and/or B-cell peptides, or microbes with or without entrapped IL-2 or microparticles containing enterotoxin. Other adjuvants known in the art are also included within the scope of the invention (see *Vaccine Design: The Subunit and Adjuvant Approach*, Chap. 7, Michael F. Powell and Mark J. Newman (eds.), Plenum Press, New York, 1995, which is incorporated herein in its entirety).

The effectiveness of an adjuvant may be determined by measuring the induction of antibodies directed against an immunogenic polypeptide containing a hSARS polypeptide epitope, the antibodies resulting from administration of this polypeptide in vaccines which are also comprised of the various adjuvants.

The polypeptides may be formulated into the vaccine as neutral or salt forms. Pharmaceutically acceptable salts include the acid additional salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccines of the invention may be multivalent or univalent. Multivalent vaccines are made from recombinant viruses that direct the expression of more than one antigen.

Many methods may be used to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

5.6 Preparation of Antibodies

Antibodies which specifically recognize a polypeptide of the invention, such as, but not limited to, polypeptides encoded by the nucleotide sequence of SEQ ID NO:1, 2, 3, 4, 5, 6, 7, 8, 9, 10 or 11, or hSARS epitope, or antigen-binding fragments thereof can be used for detecting, screening, and isolating the polypeptide of the invention or fragments thereof, or similar sequences that might encode similar proteins or polypeptides from the other organisms. Such antibodies can be used for various in vitro detection assays, including enzyme-linked immunosorbent assays (ELISA), radioimmunoassays, Western blot, etc., for the detection of a polypeptide of the invention or, preferably, hSARS, in samples, for example, a biological material, including cells, cell culture media (e.g., bacterial cell culture media, mammalian cell culture media, insect cell culture media, yeast cell culture media, etc.), blood, plasma, serum, tissues, sputum, naseopharyngeal aspirates, etc.

Antibodies specific for a polypeptide of the invention or any epitope of hSARS may be generated by any suitable method known in the art. Polyclonal antibodies to an antigen-of-interest, for example, the polypeptide encoded by the nucleotide sequence of SEQ ID NO:1, 2, 3, 4, 5, 6, 7, 8, 9, 10 or 11, or a complement thereof, can be produced by various procedures well known in the art. For example, an antigen can be administered to various host animals including, but not limited to, rabbits, mice, rats, etc., to induce the production of antisera containing polyclonal antibodies specific for the antigen. Various adjuvants may be used to increase the immunological response, depending on the host species, and include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and Corynebacterium parvum. Such adjuvants are also well known in the art. (See Section 5.5, supra).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: *Monoclonal Antibodies and T-Cell Hybridomas*, pp. 563-681 (Elsevier, N. Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, Fab and $F(ab')_2$ fragments may be produced by proteolytic cleavage of inmmunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

The antibodies of the invention or fragments thereof can be also produced by any method known in the art for the synthesis of antibodies, in particular, by chemical synthesis or preferably, by recombinant expression techniques.

The nucleotide sequence encoding an antibody may be obtained from any information available to those skilled in the art (i.e., from Genbank, the literature, or by routine cloning and sequence analysis). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., supra; and Ausubel et al., eds., 1998, Current Protocols in Molecular Biology, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule may be produced by recombinant DNA technology using techniques well known in the art as discussed in the previous sections. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression. Thus-prepared expression vector can be then introduced into appropriate host cells for the expression of the antibody. Accordingly, the invention includes host cells containing a polynucleotide encoding an antibody specific for the polypeptides of the invention or fragments thereof.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986 *Nature,* 322: 52; and Kohler, 1980 *Proc. Natl. Acad. Sci. USA* 77: 2197-9). The coding sequences for the heavy and light chains may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., 1995 *J. Immunol. Methods,* 182: 41-50; Ames et al., 1995 *J. Immunol. Methods,* 184: 177-186; Kettleborough et al., 1994 *Eur. J. Immunol.* 24: 952-958; Persic et al., 1997 *Gene* 187: 9-18; Burton et al., 1994 *Advances in Immunology* 57: 191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., 1992, *BioTechniques,* 12(6): 864-869; and Sawai et al., 1995 *AJRI,* 34: 26-34; and Better et al., 1988, *Science* 240: 1041-1043 (each of which is incorporated by reference in its entirety). Examples of techniques which can be used to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., 1988 *Science* 240: 1038-1040.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, 1985 *Science* 229: 1202; Oi et al., 1986 *BioTechniques* 4: 214; Gillies et al., 1989 *J. Immunol. Methods* 125: 191-202; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., 1988 *Nature,* 332: 323, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, 1991 *Molecular Immunology,* 28(4/5): 489498; Studnicka et al., 1994 *Protein Engineering* 7(6): 805-814; Roguska et al., 1994 *Proc Natl. Acad. Sci. USA,* 91: 969-973), and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, 1995 *Int. Rev. Immunol.,* 13: 65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Pat. No. 0 598 877; U.S. Pat. Nos. 5,413,923; 5,625,126; 5,633, 425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988 *Bio/technology,* 12: 899-903).

Antibodies fused or conjugated to heterologous polypeptides may be used in vitro immunoassays and in purification methods (e.g., affinity chromatography) well known in the art. See e.g., PCT publication Number WO 93/21232; EP 439,095; Naramura et al., 1994 *Immunol. Lett.* 39: 91-99; U.S. Pat. No. 5,474,981; Gillies et al., 1992 *PNAS* 89: 1428-1432; and Fell et al., 1991 *J. Immunol.,* 146: 2446-2452, which are incorporated herein by reference in their entireties.

Antibodies may also be attached to solid supports, which are particularly useful for immunoassays or purification of the polypeptides of the invention or fragments, derivatives, analogs, or variants thereof, or similar molecules having the similar enzymatic activities as the polypeptide of the invention. Such solid supports include, but are not limited to, glass, cellulose, polyacrylamide, nylon, polystyrene, polyvinyl chloride or polypropylene.

5.7 Pharmaceutical Compositions and Kits

The present invention encompasses pharmaceutical compositions comprising anti-viral agents of the present invention. In a specific embodiment, the anti-viral agent is an antibody which immunospecifically binds and neutralize the hSARS virus or variants thereof, or any proteins derived therefrom. In another specific embodiment, the anti-viral agent is a polypeptide or nucleic acid molecule of the invention. The pharmaceutical compositions have utility as an anti-viral prophylactic agent and may be administered to a subject where the subject has been exposed or is expected to be exposed to a virus.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987 *J. Biol. Chem.* 262: 4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In a preferred embodiment, it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non porous, or gelatinous material, including membranes, such as sialastic membranes, or fibers. In one embodiment, administration can be by direct injection at the site (or former site) infected tissues.

In another embodiment, the pharmaceutical composition can be delivered in a vesicle, in particular a liposome (see Langer, 1990 Science 249: 1527-1533; Treat et al., in Liposomes in the Therapy of Infectious Disease and Cancer, Lopez Berestein and Fidler (eds.), Liss, New York, pp. 353-365 (1989); Lopez-Berestein, ibid., pp. 317-327; see generally ibid.).

In yet another embodiment, the pharmaceutical composition can be delivered in a controlled release system. In one embodiment, a pump may be used (see Langer, supra; Sefton, 1987 CRC Crit. Ref. Biomed. Eng. 14: 201; Buchwald et al., 1980 Surgery 88: 507; and Saudek et al., 1989 N. Engl. J. Med. 321: 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983 J. Macromol. Sci. Rev. Macromol. Chem. 23: 61; see also Levy et al., 1985 Science 228: 190; During et al., 1989 Ann. Neurol. 25: 351; Howard et al., 1989, J. Neurosurg. 71: 105). In yet another embodiment, a controlled release system can be placed in proximity of the composition's target, i.e., the lung, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990 Science 249: 1527-1533).

The pharmaceutical compositions of the present invention comprise a therapeutically effective amount of a recombinant or chimeric hSARS virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2 ethylamino ethanol, histidine, procaine, etc.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the kit contains an anti-viral agent of the invention, e.g., an antibody immunospecific for the polypeptides encoded by a nucleotide sequence of SEQ ID NO:1, 2, 3, 4, 5, 6, 7, 8, 9, 10 or 11, or any hSARS epitope, or a polypeptide or protein of the present invention, or a nucleic acid molecule comprising the nucleotide sequence of SEQ ID NO:1, 2, 3, 4, 5, 6, 7, 8, 9, 10 and/or 11, alone or in combination with adjuvants, antivirals, antibiotics, analgesic, bronchodialaters, or other pharmaceutically acceptable excipients.

5.8 Demonstration of Therapeutic Utility

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed. A lower level of cytopathic effects or survival of the contacted cells indicates that the therapeutic agent is effective to treat the condition in the patient. Alternatively, instead of culturing cells from a patient, therapeutic agents and methods may be screened using established cell lines, such as FRhK-4 (fetal rhesus monkey kidney) cells which are infected by hSARS virus (see Section 6, infra). Compounds for use in therapy can be tested in suitable animal model systems prior to testing in humans, including but not limited to in rats, mice, chicken, cows, monkeys, rabbits, hamsters, etc.

The principle animal models for known in the art and widely used are known and described in the art as described above.

Further, any assays known to those skilled in the art can be used to evaluate the prophylactic and/or therapeutic utility of the combinatorial therapies disclosed herein for treatment or prevention of SARS.

5.9 Detection Assays

The present invention provides a method for detecting an antibody, which immunospecifically binds to the hSARS virus or polypeptides of the invention, in a biological sample, for example blood, serum, plasma, saliva, urine, etc., from a patient suffering from SARS. In a specific embodiment, the method comprising contacting the sample with the polypeptides encoded by the nucleotide sequence of SEQ ID NO:1, 2, 3, 4, 5, 6, 7, 8, 9, 10 and/or 11, directly immobilized on a substrate and detecting the polypeptide-bound antibody directly or indirectly by a labeled heterologous anti-isotype antibody. In another specific embodiment, the sample is contacted with a host cell which is transfected or infected by the viral vector comprising the nucleotide sequence of SEQ ID NO:1, 2, 3, 4, 5, 6, 7, 8, 9, 10 and/or 11 and the bound antibody can be detected by imrnunofluorescent assay.

The present invention provides a method for detecting the presence or absence of a polypeptide or nucleic acid of the invention in a biological sample, comprising obtaining a biological sample from various sources and contacting the sample with a compound or an agent capable of detecting an epitope or nucleic acid (e.g., mRNA, genomic DNA) of the invention such that the presence of the hSARS virus is detected in the sample. A preferred agent for detecting hSARS mRNA or genomic RNA of the invention is a labeled nucleic acid probe capable of hybridizing to mRNA or genomic RNA encoding a polypeptide of the invention or a complement thereof. The nucleic acid probe can be, for example, a nucleic acid molecule comprising or consisting of the nucleotide sequence or SEQ ID NO:1, 2, 3, 4, 5, 6, 7, 8, 9, 10 or 11, or a portion thereof, or a complement thereof, such as an oligonucleotide of at least 5, 10, 15 or 20 or more contiguous nucleotides in length and sufficient to specifically hybridize under stringent conditions to a hSARS mRNA or genomic RNA.

In another preferred specific embodiment, the presence of hSARS virus is detected in the sample by an reverse transcription polymerase chain reaction (RT-PCR) using the primers that are constructed based on a partial nucleotide sequence of the genome of hSARS virus, or a nucleotide sequence of SEQ ID NO:1, 2, 3, 4, 5, 6, 7, 8, 9, 10 or 11, a portion thereof, or a complement thereof. In a non-limiting specific embodiment, preferred primers to be used in a RT-PCR method are: 5'-TACACACCTCAGCGTTG-3' (SEQ ID NO:13) and 5'-CACGAACGTGACGAAT-3' (SEQ ID NO:14)(Poon et al., 2003, *Clin. Chem.* 49(7):1-3, which is incorporated herein by reference in its entirety), in the presence of 2.5 mM $MgCl_2$ and the thermal cycles are, for example, but not limited to, 94° C. for 8 min followed by 40 cycles of 94° C. for 1 min, 50° C. for 1 min, 72° C. for 1 min. In more preferred specific embodiment, the present invention provides a real-time quantitative PCR assay to detect the presence of hSARS virus in a biological sample by subjecting the cDNA obtained by reverse transcription of the extracted total RNA from the sample to PCR reactions using the specific primers, such as those having nucleotide sequences of SEQ ID NOS:13 and 14, and a fluorescence dye, such as SYBR® Green I, which fluoresces when bound non-specifically to double-stranded DNA. The fluorescence signals from these reactions are captured at the end of extension steps as PCR product is generated over a range of the thermal cycles, thereby allowing the quantitative determination of the viral load in the sample based on an amplification plot. Alternatively, the real-time quantitative PCR may be performed by a TaqMan® assay using specific pairs of primers. The amplified product is detected by a TaqMan® probe which is labeled by a fluorescent dye and a quencher. The preferred primers to be used are: the forward primer; 5'-GCTTAGGCCCTT TGAGAGAGACA -3' SEQ ID NO:15); and the reverse primer, 5'-GCCAATGCCAGTAG TGGTGTAAA-3' (SEQ ID NO:16). In this case, the amplified product is detected by a probe, preferably having a nucleotide sequence 5'-(TET®)CTAATGTGCCTTTCTCCCCT GATG GCA(TAMRA®)-3' (SEQ ID NO:17).

A preferred agent for detecting hSARS or the polypeptides of the invention is an antibody that specifically binds a polypeptide of the invention or any hSARS epitope, preferably an antibody with a detectable label. Antibodies can be polyclonal, or more preferably, monoclonal. An intact antibody, or a fragment thereof (e.g., Fab or F(ab')2) can be used.

The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The detection method of the invention can be used to detect mRNA, protein (or any epitope), or genomic RNA in a sample in vitro as well as in vivo. For example, in vitro techniques for detection of mRNA include northern hybridizations, in situ hybridizations, RT-PCR, and RNase protection. In vitro techniques for detection of an epitope of hSARS or the polypeptides of the invention include enzyme linked immunosorbent assays (ELISAs), Western blots, immunoprecipitations and immunofluorescence. Furthermore, in vivo techniques for detection of hSARS include introducing into a subject organism a labeled antibody directed against the polypeptide. For example, the antibody can be labeled with a radioactive marker whose presence and location in the subject organism can be detected by standard imaging techniques, including autoradiography.

In a specific embodiment, the methods further involve obtaining a control sample from a control subject, contacting the control sample with a compound or agent capable of detecting hSARS, e.g., a polypeptide of the invention or mRNA or genomic RNA encoding a polypeptide of the invention, such that the presence of hSARS or the polypeptide or mRNA or genomic RNA encoding the polypeptide is detected in the sample, and comparing the presence of hSARS or the polypeptide or mRNA or genomic RNA encoding the polypeptide in the control sample with the presence of hSARS, or the polypeptide or mRNA or genomic RNA encoding the polypeptide in the test sample.

The invention also encompasses kits for detecting the presence of hSARS or a polypeptide or nucleic acid of the invention in a test sample. The kit, for example, can comprise a labeled compound or agent capable of detecting hSARS or the polypeptide or a nucleic acid molecule encoding the polypeptide in a test sample and, in certain embodiments, a means for determining the amount of the polypeptide or mRNA in the sample (e.g., an antibody which binds the polypeptide or an oligonucleotide probe which binds to DNA or mRNA encoding the polypeptide). Kits can also include instructions for use.

For antibody-based kits, the kit can comprise, for example: (1) a first antibody (e.g., attached to a solid support) which binds to a polypeptide of the invention or hSARS epitope; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or to a sequence within the hSARS genome or (2) a pair of primers useful for amplifying a nucleic acid molecule containing an hSARS sequence. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for use.

5.10 Screening Assays to Identify Anti-Viral Agents

The invention provides methods for the identification of a compound that inhibits the ability of hSARS virus to infect a host or a host cell. In certain embodiments, the invention provides methods for the identification of a compound that reduces the ability of hSARS virus to replicate in a host or a host cell. Any technique well-known to the skilled artisan can be used to screen for a compound that would abolish or reduce the ability of hSARS virus to infect a host and/or to replicate in a host or a host cell.

In certain embodiments, the invention provides methods for the identification of a compound that inhibits the ability of hSARS virus to replicate in a mammal or a mammalian cell. More specifically, the invention provides methods for the identification of a compound that inhibits the ability of hSARS virus to infect a mammal or a mammalian cell. In certain embodiments, the invention provides methods for the identification of a compound that inhibits the ability of hSARS virus to replicate in a mammalian cell. In a specific embodiment, the mammalian cell is a human cell.

In another embodiment, a cell is contacted with a test compound and infected with the hSARS virus. In certain embodiments, a control culture is infected with the hSARS virus in the absence of a test compound. The cell can be contacted with a test compound before, concurrently with, or subsequent to the infection with the hSARS virus. In a specific embodiment, the cell is a mammalian cell. In an even more specific embodiment, the cell is a human cell. In certain embodiments, the cell is incubated with the test compound for at least 1 minute, at least 5 minutes at least 15 minutes, at least 30 minutes, at least 1 hour, at least 2 hours, at least 5 hours, at least 12 hours, or at least 1 day. The titer of the virus can be measured at any time during the assay. In certain embodiments, a time course of viral growth in the culture is determined. If the viral growth is inhibited or reduced in the presence of the test compound, the test compound is identified as being effective in inhibiting or reducing the growth or infection of the hSARS virus. In a specific embodiment, the compound that inhibits or reduces the growth of the hSARS virus is tested for its ability to inhibit or reduce the growth rate of other viruses to test its specificity for the hSARS virus.

In one embodiment, a test compound is administered to a model animal and the model animal is infected with the hSARS virus. In certain embodiments, a control model animal is infected with the hSARS virus without the administration of a test compound. The test compound can be administered before, concurrently with, or subsequent to the infection with the hSARS virus. In a specific embodiment, the model animal is a mammal. In an even more specific embodiment, the model animal can be, but is not limited to, a cotton rat, a mouse, or a monkey. The titer of the virus in the model animal can be measured at any time during the assay. In certain embodiments, a time course of viral growth in the culture is determined. If the viral growth is inhibited or reduced in the presence of the test compound, the test compound is identified as being effective in inhibiting or reducing the growth or infection of the hSARS virus. In a specific embodiment, the compound that inhibits or reduces the growth of the hSARS in the model animal is tested for its ability to inhibit or reduce the growth rate of other viruses to test its specificity for the hSARS virus.

6. EXAMPLES

The following examples illustrate the use of siRNAs for preventing or treating SARS infection. These examples should not be construed as limiting.

6.1 Materials and Methods siRNA (1) siRNAs targeting the replicase 1A region of SCoV.

Because of the conserved nature of 5'-sequence, we designed six 21- and 22-mer siRNAs targeting different sites of the replicase 1A region (FIGS. 1A and 1B). Double stranded siRNAs were synthesized by GENSET SA Ltd. (Paris, France). The sense strands of SARSi-1 (SEQ ID NO:1), SARSi-2 (SEQ ID NO:2), SARSi-3 (SEQ ID NO:3), SARSi-4 (SEQ ID NO:4), SARSi-5 (SEQ ID NO:5) and SARSi-6 (SEQ ID NO:6) correspond to the coronavirus nucleotide sequences, 512 to 531, 586 to 604, 916 to 934, 1194 to 1213, 3028 to 3046 and 5024 to 5042, respectively.

(2) siRNAs targeting the structural genes of SCoV.

Five 21-, 22- and 23-mer siRNAs targeting one site of each of the S glycoprotein gene, E protein gene and N protein gene and two sites of the M protein gene of SCoV, respectively (FIGS. 4A and 4B), were prepared according to the method described above. The sense strands of SARSi-7 (SEQ ID NO:7), SARSi-8 (SEQ ID NO:8), SARSi-9 (SEQ ID NO:9), SARSi-10 (SEQ ID NO:10) and SARSi-11 (SEQ ID NO:11) correspond to the coronavirus nucleotide sequences, 23165 to 23184, 26128 to 26148, 28663 to 28682, 26652 to 26671 and 26575 to 26595, respectively.

In addition, GL2i (5'-CGUACGCGGAAUACUUCGATT-3'; SEQ ID NO:12), a siRNA targeting luciferase mRNA (Elbashir, S M, et al. Duplexes of 21-nucleotide RNAs mediate RNA interference in cultured mammalian cells. *Nature* 2001; 411: 494-498), was used as unrelated siRNA control. In some experiments, SARSi-4, which showed the most potent siRNA targeting rep as described above, was used as positive control.

Cell Culture, Transfection and Viral Infection

Unlike other human coronaviruses, it is possible to grow the SARS-associated coronavirus in monkey cells (Peiris, J S, et al., 2003, Coronavirus as a possible cause of severe acute respiratory syndrome, *Lancet* 361: 1319-1325). The anti-SARS activities of the six siRNA were tested in monkey kidney cells (FRhk-4 cells).

In general, about 3000 cells of FRhk-4 which had been cultured in MEM medium with 10% FBS were seeded in each of 96 well and transfected with 200 nM siRNA using Oligofectamine (Invitrogen, MD) according to the manufacturer's instructions. Four hours post-transfection, 10% fetal bovine serum (FBS) was added to the culture medium. After incubation for additional four hours (total 8-hour incubation for SARSi1-6 and 6-hour incubation for SARSi7-12, post-transfection), the medium was removed, and the cells were washed once with PBS, and infected with one isolate of SARS-associated coronavirus (GZ50 strain) in PBS buffer at multiplicity of infection (MOI) 0.05 for one hour. The cells were then washed twice with MEM medium and cultured in the same medium containing 1% FBS for 36 hours for SARSi1-6 and 24 hours for SARSi7-12. For SARSi1-6, pictures were taken before and after immunostaining (FIG. 2) using phase-contrast microscopy and fluorescent microscopy, respectively. Cytopathic effects (CPE) of the infected cells with or without SARSi7-12 were also recorded using phase-contrast microscopy (FIG. 5).

To test the effects of SARSi-4 on the replication of different coronavirus strains, additional three (3) strains (GZ34 strain isolated from SARS patient in Guandong Province; and HKR1 and HKR2 strains isolated in Hong Kong, respectively) were purified and used to infect FRhk-4 cells (see FIG. 3B).

Immunostaining

After infection with coronavirus for 36 hours, the cells were fixed with −20° C. ethanol for 10 min and coronavirus antigens were detected by indirect immunoflorescence assay (IFA) as described by Peiris et al (Coronavirus as a possible cause of severe acute respiratory syndrome. Lancet 2003; 361: 1319-1325). Briefly, after the cells were fixed with ethanol, anti-SARS sera from SARS patients were added and incubated for 30 min at room temperature. The cells were then washed with PBS 4 times, 5 min each, and stained with FITC-labeled secondary antibody (St. Cruz, Calif. USA).

Quantitative Real-time PCR

The total RNA was isolated 36 hours after infection and reverse-transcription was applied. Real-time PCR was performed as described previously (Poon, LLM, et al., 2003, Rapid Diagnosis of a Coronavirus Associated with Severe Acute Respiratory syndrome (SARS). *Clin. Chem.* 49(7): 1-3). Briefly, the cells in each well (about 3,000 cells) were washed twice with PBS, and total RNA was extracted using RNeasy Mini Kit (Qiagen, Germany) in accordance with the manufacturer's instructions. Reverse-transcription was performed using random hexamers with the ThermoScript™ RT system (Invitrogen, Calif.).

Intracellular viral RNA was quantified using quantitative RT-PCR either by method A (see FIG. 3A) or B (FIGS. 6A and 6C). In method A, FastStart DNA Master SYBR Green I fluorescence reaction (Roche, Ind.) was used in the PCR assay. Briefly, 2 μl of cDNA was amplified in 20 μl containing, per liter, 3.5 mmol of $MgCl_2$, 0.25 μmol of forward primer (coro3: 5'-TACACACCTCAGCGTTG-3'; SEQ ID NO:13), and 025 μmol of reverse primer (coro4: 5'-CACGAACGT-GACGAAT-3'; SEQ ID NO:14). Reactions were performed in a LightCycler® (Roche) with the following conditions: 10 min at 95° C.; followed by 5-cycles of 95° C. for 10 sec; and 72° C. for 9 sec. Plasmids containing the target sequence were used as positive controls. Fluorescence signals from these reactions were captured at the end of the extension step in each cycle. To determine the specificity of the assay, PCR products were subjected to melting curve analysis at the end of the assay (65° to 95° C.; 0.1° C./sec) (data not shown).

In method B, the forward primer (5'-GCTTAGGC-CCTTTGAGAGAGACA-3'; SEQ ID NO:15), the reverse primer (5'-GCCAATGCCAGTAGTGGTGTAAA-3'; SEQ ID NO:16) and the fluorescent probe [5'-(TET®)CTAATGT-GCCTTTCTCCCCTGATGGCA (TAMRA®)-3'; SEQ ID NO:17] which hybridized to the 5'-region of S gene, was used for real-time PCR (TaqMan® technology). Forward and reverse primers (final concentration 900 nM), the fluorescent probe (final concentration 250 nM) and 2 μl of the RT product (template) were mixed with Master Mix (Applied Biosystems, USA). The real-time quantification was carried out using ABI PRISM®7900 HT Sequence Detection System. PCR conditions employed were: 50° C. for 5 min; 95° C. for 10 min; then 40 cycles of 95° C. for 15 sec; and 61° C. for 1 min.

In some experiments, the total intracellular RNA from infected cells were isolated at different time points and quantified for viral genomic RNA copies (He, M. L., 2003, *Jama* 290:2665-2666; which is incorporated herein by reference in its entirety) (see FIG. 6A).

To test whether the anti-viral activities of the siRNAs are dose-dependent, FRhk-4 cells were transfected with different amounts of the siRNAs, respectively. To normalize the transfection efficiency, GL2i was used as a carrier and the final concentration of siRNAs (SARSi+GL2i) was maintained as 200 nM in the culture media (see FIG. 6C).

Back Titration of Virus In the Culture Media

The effects of siRNAs on viral titers were determined by back titration experiments in the culture media 24-hour postinfection. Viral titer is a parameter of live viruses, which reflects the actual viral genome replication, packaging and secretion. Briefly, viral particles released into the culture medium were quantified using a CPE-based $TCID_{50}$ test. Culture supernatant collected from SARS-CoV-infected cells 24 hours after viral infection was serially diluted at 10-fold with 1%-MEM and inoculated into FRhK-4-cells in 96-well plates. Results were evaluated after 3 days of culture under phase-contrast microscopy, and viral titers were calculated (FIG. 6B).

Synergistic Effects by Combinations of siRNAs

To further test the antiviral activities at low dosage and possible synergistic effects, the inhibitory effect of the siRNA at 10 nM was first studied (the left half of FIG. 6D). In some experiments, the combinations of two different siRNAs (i.e., SARSi-4/7; SARSi-4/8; SARSi-4/9; SARSi-7/8; and SARSi-7/9) at equal amount, keeping the total siRNA concentration at 10 nM in the culture media (i.e., 5 nM each of two siRNAs), were tested by back titration (see the right half of FIG. 6D).

6.2 Results and Discussion

FRhk-4 cells infected with coronavirus with or without GL2i exhibited a significant morphological change with cytopathic effect (CPE, FIGS. 2-B, 5-II and 5-III) in comparison with the uninfected negative control (FIGS. 2-A and 5-I). Uninfected cells were flattened, whereas the infected cells became refractile and rounded up, and were floating away or dead. No toxicity or CPE was observed when cells were transfected with siRNA alone (data, except for GL2i, not shown; for GL2i, see FIG. 5-III). Transfection with SARSi-2, SARSi-3 and SARSi-4 markedly inhibited the CPE caused by viral infection and replication (FIGS. 2-D, 2-E and 2-F, respectively), whereas SARSi-1, SARSi-5 and SARSi-6 were less effective (FIGS. 2-C, 2-G and 2-H, respectively), judged by morphological changes. The cells transfected with SARSi-7 through 11 were also protected from CPE (FIGS. 5-VI through 5-X, respectively), demonstrating that siRNAs that target structural genes also exhibit anti-SARS activities.

The results were further confirmed by immunostaining with antibody against coronavirus antigens (FIGS. 2-I through 2-P). These findings clearly demonstrated the inhibition of coronavirus infection and replication by siRNAs (SARSi-2, 3, 4, 7, 8, 9, 10, and 11).

To determine the relative efficacy of their anti-coronavirus activities, the viral titers were determined by quantitative RT-PCR as described previously (Poon et al., supra.). As shown in FIG. 3A, among siRNAs targeting the replicase 1A region, SARSi-4 was the most effective siRNA, against the coronavirus, which almost completely inhibited coronavirus infection and replication, followed by SARSi-2 and SARSi-3. The viral titer was reduced by 92% by SARi-4, 89% by SARSi-2 and 85% by SARSi-3, but by only 50% to 65% by the other three siRNAs. The siRNA specifically targeting on luciferase mRNA (GL2i, see Elbashir, S M, et al. Duplexes of 21-nucleotide RNAs mediate RNA interference in cultured mammalian cells. *Nature* 2001; 411:494-498) did not exhibit anti-SARS activity (FIGS. 3A, 5-IV, 6A and 6B). SARSi-4 was also most effective in anti-SARS viral replication when compared with those targeting the structural genes (i.e., SARSi7 through SARSi-11) in the study for the time course of viral replication in the transfected cells (see FIG. 6A). The results on the inhibition of coronavirus replication in FIGS. 2 and 3A as well as FIGS. 5 and 6B were consistent.

It is known that RNA viruses including coronavirus are usually associated with rapid evolution and frequent mutations after interspecies transmission (Domingo, E, et al. RNA virus mutations and fitness for survival. *Annu Rev Microbiol.* 1997; 51:151-178).

We have isolated and purified four different stains of coronavirus, i.e., GZ34 stain, GZ50 stain, HKR1 stain and HKR2 stain, from SARS patients in Guangdong Province and Hong Kong. The effects of SARSi-4 on the replication of different coronavirus stains were examined using the methods as described, supra.

SARSi-4 markedly inhibited the replication of all three other strains (FIG. 3B). Therefore, the siRNAs targeting on the replicase gene will be the best choice for the development of a broad range of anti-SARS drugs. Based on the present studies, SARSi-4 offers promise for development into a new anti-SARS drug. Since the siRNA targets on the conserved RNA sequence of replicase region, SARSi-4 can be used for the treatment of different subtypes of coronavirus infections.

Since the use of combination drugs often exhibits synergistic effects, thereby allowing the lower dosages, the same possibility was explored by combining siRNAs that target different gene sites. The inhibitory effect of individual siRNAs (SARSi-4, 7, 8, 9 and 10) used alone was lower at 10 nM than at 200 nM. The viral titer was reduced 5-fold by SARSi-4, 6-fold by SARSi-8, and 1-fold by SARSi-7, 9 and 10 without carrier siRNA (see the left half of FIG. 6D). No synergistic effects were observed when two or three effective siRNAs targeting rep gene were combined (He, M. L. et al., 2003, *JAMA* 290:2665-2666, which is incorporated herein by reference in its entirety). However, the viral titers were reduced 18-fold by the combinations of SARSi4/7 and SARSi-7/8, respectively and between 6-fold and 12-fold by the combinations of SARSi-4/8, 4/9 and 7/9, respectively. Thus, we demonstrated that siRNAs targeting functionally distinct genes exhibit synergistic effect even at the lower dosages. The enhanced antiviral effects of siRNAs used in combination at the low dosage indicate a high possibility of their use in clinical applications with high efficacy and reduced toxicity. As siRNA undergoes totally different metabolism from those of other types of antiviral drugs, it may be used alone or in combination with other anti-viral agents, such as interferon-beta, to achieve more effective treatment for SARS.

Previous studies have reported an almost complete inhibition of HBV replication by siRNAs/shRNAs (He et al., submitted). Other examples of inhibition of gene expression may be found in Kapadia, S B, et al. Interference of hepatitis C virus RNA replication by short interfering RNAs. *Proc. Natl. Acad. Sci. USA* 2003; 100: 2014-2018; Randall, G, et al. Clearance of replicating hepatitis C virus replicon RNAs in cell culture by small interfering RNAs. *Proc. Natl. Acad. Sci. USA* 2003; 100: 235-240; Wilson, J A, et al. RNA interference blocks gene expression and RNA synthesis from hepatitis C replicons propagated in human liver cells. *Proc. Natl. Acad. Sci. USA*. 2003; 100: 2783-2788; Jacque, J M, et al. Modulation of HIV-1 replication by RNA interference. *Nature* 2002; 418: 435-438; Lee, N S, et al. Expression of small interfering RNAs targeted against HIV-1 rev transcripts in human cells. *Nat. Biotechnol.* 2002; 20: 500-505; and Novina, C D, et al. siRNA-directed inhibition of HIV-1 infection. *Nat. Med.* 2002; 8: 681-686.

7. MARKET POTENTIAL

The recent worldwide outbreak of SARS has posed the urgent need for effective vaccines and/or drugs for prevention and treatment of SARS. The siRNA disclosed herein are particularly useful for inhibiting SARS infection and replication in humans and are good candidates for clinical and research applications.

8. EQUIVALENTS

Those skilled in the art will recognize, or be able to ascertain many equivalents to the specific embodiments of the invention described herein using no more than routine experimentation. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed:

1. An isolated nucleic acid molecule consisting of the nucleotide sequence of SEQ ID NO:2 and/or the complement thereof.

2. An isolated double-stranded nucleic acid molecule, wherein the nucleotide sequence of a first stand consists of the nucleotide sequence of SEQ ID NO:2 and the nucleotide sequence of a second strand is complementary to the nucleotide sequence of the first strand.

3. The nucleic acid molecule of claim 2, wherein said nucleic acid molecule is a RNA.

* * * * *

UNITED STATES PATENT AND TRADEMARK OFFICE
CERTIFICATE OF CORRECTION

PATENT NO. : 7,429,656 B2  Page 1 of 1
APPLICATION NO. : 11/452267
DATED : September 30, 2008
INVENTOR(S) : Kung et al.

It is certified that error appears in the above-identified patent and that said Letters Patent is hereby corrected as shown below:

Column 23,
Line 42 "28(4/5): 489498" should read --28(4/5): 489-498--.

Column 32,
Line 11 "and 025 μmol" should read --and 0.25 μmol--.

Signed and Sealed this

Twenty-first Day of April, 2009

JOHN DOLL
*Acting Director of the United States Patent and Trademark Office*

SEQUENCE LISTING

<160> NUMBER OF SEQ ID NOS: 17

<210> SEQ ID NO 1
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-1
<220> FEATURE:
<223> OTHER INFORMATION: Description of Artificial Sequence: Synthetic
      oligonucleotide

<400> SEQUENCE: 1
gugaacucac ucgugagcuc tt                                          22

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-2
<220> FEATURE:
<223> OTHER INFORMATION: Description of Artificial Sequence: Synthetic
      oligonucleotide

<400> SEQUENCE: 2
guacccucuu gauugcauct t                                           21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-3
<220> FEATURE:
<223> OTHER INFORMATION: Description of Artificial Sequence: Synthetic
      oligonucleotide

<400> SEQUENCE: 3
gagucgaaga gaggugucut t                                           21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-4
<220> FEATURE:
<223> OTHER INFORMATION: Description of Artificial Sequence: Synthetic
      oligonucleotide

<400> SEQUENCE: 4
gcacuugucu accuugaugt t                                           21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-5
<220> FEATURE:
<223> OTHER INFORMATION: Description of Artificial Sequence: Synthetic
      oligonucleotide

```
<400> SEQUENCE: 5
ccuccagaug aggaagaagt t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-6
<220> FEATURE:
<223> OTHER INFORMATION: Description of Artificial Sequence: Synthetic
      oligonucleotide

<400> SEQUENCE: 6
gguguuucca uuccaugugt t                                              21

<210> SEQ ID NO 7
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-7
<220> FEATURE:
<223> OTHER INFORMATION: Description of Artificial Sequence: Synthetic
      oligonucleotide

<400> SEQUENCE: 7
cacugauucc guucgagauc tt                                             22

<210> SEQ ID NO 8
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-8
<220> FEATURE:
<223> OTHER INFORMATION: Description of Artificial Sequence: Synthetic
      oligonucleotide

<400> SEQUENCE: 8
cguuucggaa gaaacaggua ctt                                            23

<210> SEQ ID NO 9
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-9
<220> FEATURE:
<223> OTHER INFORMATION: Description of Artificial Sequence: Synthetic
      oligonucleotide

<400> SEQUENCE: 9
caagccucuu cucgcuccuc tt                                             22

<210> SEQ ID NO 10
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-10
<220> FEATURE:
<223> OTHER INFORMATION: Description of Artificial Sequence: Synthetic
```

-continued

```
oligonucleotide

<400> SEQUENCE: 10
guggcuuagc uacuucguug tt                                            22

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide SARSi-11
<220> FEATURE:
<223> OTHER INFORMATION: Description of Artificial Sequence: Synthetic
      oligonucleotide

<400> SEQUENCE: 11
ugcuugcugc ugucuacagt t                                             21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide GL2i
<220> FEATURE:
<223> OTHER INFORMATION: Description of Artificial Sequence: Synthetic
      oligonucleotide

<400> SEQUENCE: 12
cguacgcgga auacuucgat t                                             21

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 13
tacacacctc agcgttg                                                  17

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 14
cacgaacgtg acgaat                                                   16

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 15
gcttaggccc tttgagagag aca                                           23

<210> SEQ ID NO 16
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 16
gccaatgcca gtagtggtgt aaa                                              23

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 17
ctaatgtgcc tttctcccct gatggca                                          27
```